US009511117B2

United States Patent
Ward et al.

(10) Patent No.: US 9,511,117 B2
(45) Date of Patent: Dec. 6, 2016

(54) TREATMENT OF MUSCULAR CONDITIONS AND MUSCULAR DYSTROPHIES

(71) Applicants: Christopher W. Ward, Baltimore, MD (US); Ramzi Khairallah, Chicago, IL (US)

(72) Inventors: Christopher W. Ward, Baltimore, MD (US); Ramzi Khairallah, Chicago, IL (US)

(73) Assignee: University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 14/284,736

(22) Filed: May 22, 2014

(65) Prior Publication Data
US 2014/0256644 A1 Sep. 11, 2014

Related U.S. Application Data

(60) Provisional application No. 61/562,527, filed on Nov. 22, 2011.

(51) Int. Cl.
| | |
|---|---|
| A61K 38/12 | (2006.01) |
| A61K 38/17 | (2006.01) |
| A61K 45/06 | (2006.01) |
| A61K 31/165 | (2006.01) |
| A61K 31/12 | (2006.01) |
| A61K 31/4178 | (2006.01) |

(52) U.S. Cl.
CPC ........... *A61K 38/1767* (2013.01); *A61K 31/12* (2013.01); *A61K 31/165* (2013.01); *A61K 31/4178* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 8,771,692 B2 * | 7/2014 | Brandan et al. ........... | 424/139.1 |
| 2006/0280812 A1 * | 12/2006 | Carlson et al. ............... | 424/725 |
| 2010/0034806 A1 | 2/2010 | Dietz | |
| 2012/0184491 A1 * | 7/2012 | Sachs et al. ................. | 514/13.5 |

FOREIGN PATENT DOCUMENTS

EP 2305679 A1 4/2011

OTHER PUBLICATIONS

Alderton, J et al. (2000) How Calcium Influx through Calcium Leak Channels is Responsible for the Elevated Levels of Calcium-dependent Proteolysis in Dystrophic Myotubes. Trends in Cardiovascular Medicine. vol. 10: pp. 268-272; entire document.
Allen, DG et al. (2004) Skeletal Muscles Function: Role of Ionic Changes in Fatigue, Damage and Disease. Clinical and Experimental Pharmacology and Physiology. vol. 31: pp. 485-493; entire document.
Allen, DG et al. (2010) Stretch-Induced Membrane Damage in Muscle: Comparison of Wild-Type and mdx Mice. Muscle Biophysics: From Molecules to Cells: Advances in Experimental Medicine and Biology. vol. 682: pp. 297-313; entire document.
Allen, DG et al. (2010) Calcium and the Damage Pathways in Muscular Dystrophy. Can. J. Physiol. Pharmacol. vol. 88: pp. 83-91; entire document.
Anders, S et al. (2010) Differential Expression Analysis for Sequence Count Data. Genome Biology. vol. 11: pp. 1-12; entire document.
Bae, C et al. (2011) The Mechanosensitive Ion Channel Piezo1 is Inhibited by the Peptide GsMTx4. Biochemistry. vol. 50: pp. 6295-6300; entire document.
Best, A et al. (1996) The Ras-related GTPase Rac1 Binds Tubulin. J. Biol. Chem. vol. 271: pp. 3756-3762; entire document.
Bhandarkar, SS et al. (2009) Fulvene-5 Potently Inhibits NADPH Oxidase 4 and Blocks the Growth of Endothelial Tumors in Mice. J. Clin. Invest. vol. 119: pp. 2359-2365; entire document.
Blaauw, B et al. (2008) Akt Activation Prevents the Force Drop Induced by Eccentric Contractions in Dystrophin-deficient Skeletal Muscle. Human Molecular Genetics. vol. 17: pp. 3686-3696; entire document.
Bogeski, I et al. (2011) Redox Regulation of Calcium Ion Channels: Chemical and Physiological Aspects. Cell Calcium. vol. 50: pp. 407-423; entire document.
Bogeski, I et al. (2010) Differential Redox Regulation of ORAI Ion Channels: A Mechanism to Tune Cellular Calcium Signaling. Science Signaling. vol. 3: pp. 1-16; entire document.
Canato, M et al. (2010) Mechanical and Electrophysiological Properties of the Sarcolemma of Muscle Fibers in Two Murine models of Muscle Dystrophy: Col6a1-/- and Mdx. Journal of Biomedicine and Biotechnology. vol. 2010: pp. 1-13; entire document.
Chen, YW et al. (2005) Early Onset of Inflammation and Later Involvement of TGFb in Duchene Muscular Dystrophy. Neurology. vol. 65: pp. 826-834; entire document.
Cohn, RD et al. (2007) Angiotensin II Type 1 Receptor Blockade Atenuates TGF-b-induced Failure of Muscle Regeneration in Multiple Myopathic States. Nat. Med. vol. 13: pp. 204-210; entire document.
Collet, C et al. (2003) Intramembrane Charge Movement and L-Type Calcium Current in Skeletal Muscle Fibers Isolated from Control and mdx Mice. Biophysical Journal. vol. 84: pp. 251-265; entire document.
Coste, B et al. (2010) Piezo1 and Piezo2 are Essential Components of Distinct Mechanically-Activated Cation Channels. Science. vol. 330: pp. 55-60; entire document.
Defranchi, E et al. (2005) Imaging and Elasticity Measurements of the Sarcolemma of Fully Differentiated Skeletal Muscle Fibres. Microscopy Research and Technique. vol. 67: pp. 27-35; entire document.

(Continued)

*Primary Examiner* — John Ulm
(74) *Attorney, Agent, or Firm* — Benjamin Aaron Adler

(57) ABSTRACT

The present invention provides methods for improving muscular function or treating a muscular disorder in an individual by administering to the individual a pharmacologically effective amount of a compound that inhibits microtubule-dependent NADPH Oxidase 2 reactive oxygen species signaling production. In addition compounds that block sarcolemmal $Ca^{2+}$ channel activation and/or renin-angiotensin signaling may be administered with the inhibitor of microtubule-dependent NADPH Oxidase 2 reactive oxygen species signaling production.

16 Claims, 13 Drawing Sheets

(56) References Cited

OTHER PUBLICATIONS

Dorsey, SG et al. (2011) Genetic Deletion of trkB.T1 Increases Neuromuscular Function. Am. J. Physiol. Cell Physiol. vol. 302: pp. C141-C153; entire document.

Espinosa, A et al. (2006) Myotube Depolarization Generates Reactive Oxygen Species through NAD(P)H Oxidase; ROS-Elicited Ca2+ Stimulates ERK, CREB, Early Genes. Journal of Cellular Physiology. vol. 209: pp. 379-388; entire.

Fernandes, JJ et al. (2005) A Dominant Negative Form of Rac1 Affects Myogenesis of Adult Thoracic Muscles in *Drosophila*. Developmental Biology. vol. 285: pp. 11-27; entire document.

Grange, RW et al. (2002) Fast-twitch Skeletal Muscles of Dystrophic Mouse Pups are Resistant to Injury from Acute Mechanical Stress. Am. J. Physiol. Cell Physiol. vol. 283: pp. C1090-C1101; entire document.

Grody, WW et al.. (2010) Colchicine's Other Indication—Effect of FDA Action. N. Engl. J. Med. vol. 363: pp. 2267-2268; entire document.

Hashmoto-Komatsu, A et al. (2011) Angiotensin II Induces Microtubule Reorganization Mediated by a Deacetylase SIRT2 in Endothelial Cells. Hypertension Research. vol. 34: pp. 949-956; entire document.

Hidalgo, C et al. (2006) A Transverse Tubule NADPH Oxidase Activity Stimulates Calcium Release from Isolated Triads via Ryanodine Receptor Type 1 S-Glutathionylation. The Journal of Biological Chemistry. vol. 281: pp. 26473-26482; entire document.

Hoffman, EP et al. (1987) Dystrophin: The Protein Product of the Duchenne Muscular Dystrophy Locus. Cell. vol. 51: pp. 919-928; entire document.

Ingber, DE et al. (2008) Tensegrity-Based Mechanosensing from Macro to Micro. Prog. Biophyc. Mol. Biol. vol. 97: pp. 163-179; entire document.

Ingber, DE et al. (2008) Tensegrity and Mechanotransduction. J. Bodyw. Mov. Ther. vol. 12: pp. 198-200; entire document.

Iribe, G et al. (2009) Axial Stretch of Rat Single Ventricular Cardiomyocytes Causes an Acute and Transient Increase in Ca2+ Spark Rate. Circ. Res. vol. 104: pp. 787-795; entire document.

Isaeva, EV et al. (2003) Metabolic Regulation of Ca2+ Release in Permeabilized Mammalian Skeletal Muscle Fibers. J. Physiol. vol. 547: pp. 453-462; entire document.

Isaeva, EV et al. (2005) Mitochondrial Redox State and Ca2+ Sparks in Permeabilized Mammalian Skeletal Muscle. J. Pysiol. vol. 565: pp. 855-872; entire document.

Langevin, HM et al. (2011) Fibroblast Cytoskeletal Remodeling Contributes to Connective Tissue Tension. J. Cell Physiol. vol. 226: pp. 1166-1175; entire document.

Marchand, EM et al. (2001) Calcium Homeostasis and Cell Death in Sol8 Dystrophin-Deficient Cell Line in Culture. Cell Calcium. vol. 29: pp. 85-96; entire document.

McCain, ML et al. (2011) Mechanotransduction: The Role of Mechanical Stress, Myocyte Shape, and Cytoskeletal Architecture on Cardiac Function. Eur. J. Physiol. vol. 462: pp. 89-104; entire document.

Millay, DP et al. (2009) Calcium Influx is Sufficient to Induce Muscular Dystrophy Through a TRPC-Dependent Mechanism. PNAS. vol. 106: pp. 19023-19028; entire document.

NG, R et al. (2008) Poloxamer 188 Reduces the Contraction-Induced Force Decline in Lumbrical Muscles from mdx Mice. Am. J. Physiol. Cell Physiol. vol. 295: pp. C146-C150; entire document.

Nishiyama, A et al. (2007) Two Novel Missense Mutations in the Myostatin Gene Identified in Japanese Patients with Duchenne Muscular Dystrophy. BMC Medical Genetics. vol. 8: pp. 1-9; entire document.

Ogata, H et al. (2009) Beneficial Effects of Beta-Blockers and Angiotensin-Converting Enzyme Inhibitors in Duchenne Muscular Dystrophy. Journal of Cardiology. vol. 53: pp. 72-78; entire document.

Pegoraro, E et al. (2010) SPP1 Genotype is a Determinant of Disease Severity in Duchenne Muscular Dystrophy. Neurology. vol. 76: pp. 219-226; entire document.

Prins, KW et al. (2009) Dystrophin is a Microtubule-Associated Protein. The Journal of Cell Biology. vol. 186: pp. 363-369; entire document.

Prosser, BL et al. (2011) X-ROS Signaling: Rapid Mechano-Chemo Transduction in Heart. Science. vol. 333: pp. 1440-1445; entire document.

Devillard, L. et al. Tubulin ligands suggest a microtubule-NADPH oxidase relationship in postischemic cardiomyocytes. Eur. J. Pharmacol. 2006; vol. 548(1-3): pp. 64-73 [online] Retrieved from PubMed, PMID: 16973157; abstract, only.

Okamura, N et al. Cooperation of cytochalasin D and antimicrotubular agents in stimulating superoxide anion production in polymorphonuclear leukocytes. J. Biochem., 1980; vol. 88(1): pp. 139-144; abstract.

Kelly, KA et al. NOX2 inhibition with apocynin worsens stroke outcome in aged rats. Brain Res., 2009; vol. 1292: pp. 165-172. doi: 10.1016/j.brainres.2009.07.052. Epub Jul. 25, 2009; abstract.

Yeung, EW et al. Effects of stretch-activated channel blockers on [Ca2+]i and muscle damage in the mdx mouse. J. Physiol., 2005; vol. 562(Pt2): pp. 367-380. Epub Nov. 4, 2004; abstract.

Spurney, CF et al. Dystrophin-deficient cardiomyopathy in mouse: Expression of Nox4 and Lox are associated with fibrosis and altered functional parameters in the heart. Neuromuscul. Disord., 2008; vol. 18(5): pp. 371-381. doi: 10.1016/j.nmd.2008.03.008. Epub Apr. 25, 2008. Author manuscript; available in PMC May 1, 2009; abstract; p. 2; p. 6; p. 9.

Rey, FE et al. (2001) Novel Competitive Inhibitor of NAD(P)H Oxidase Assembly Attenuates Vascular O2- and Systolic Blood Pressure in Mice. Circ. Res. vol. 89: pp. 408-414; entire document.

Spencer, MJ et al. (1997) Myonuclear Apoptosis in Dystrophic mdx Muscle Occurs by Perforin-mediated Cytotoxicity. J. Clin. Invest. vol. 99: pp. 2745-2751; entire document.

Stamenovic, D et al. (2002) Cell Prestress. II Contribution of Microtubules. Am. J. Physiol. Cell Physiol. vol. 282: pp. C617-C624; entire document.

Stiber, JA et al. (2008) Mice Lacking Homer 1 Exhibit a Skeletal Myopathy Characterized by Abnormal Transient Receptor Potential Channel Activity. Molecular and Cellular Biology. vol. 28: pp. 2637-2647; entire document.

Stolk, J et al. (1994) Characteristics of the Inhibition of NADPH Oxidase Activation in Neutrophils by Apocynin, a Methoxy-substituted Catechol. Am. J. Respir. Cell Mol. Biol. vol. 11: pp. 95-102; entire document.

Stroth, U et al. (1998) Angiotensin II and NGF Differentially Influence Microtubule Proteins in PC12W Cells: Role of the AT2 Receptor. Molecular Brain Research. vol. 53: pp. 187-195; entire document.

Suchyna, TM et al. (2004) Bilayer-Dependent Inhibition of Mechanosensitive Channels by Neuroactive Peptide Enantiomers. Nature. vol. 430: pp. 235-240; entire document.

Suchyna, TM et al. (2007) Mechanosensitive Channel Properties and Membrane Mechanics in Mouse Dystrophic Myotubes. J. Physiol. vol. 581: pp. 369-387; entire document.

Sun, G et al. (2009) Intramuscular Renin-angiotensin System is Activated in Human Muscular Dystrophy. Journal of the Neurological Sciences. vol. 280: pp. 40-48; entire document.

Turner, PR et al. (1993) Proteolysis Results in Altered Leak Channel Kinetics and Elevated Free Calcium in mdx Mice. J. Membrane Biol. vol. 133: pp. 243-251; entire document.

Tutdibi, O et al. (1999) Increased Calcium Entry into Dystrophin-deficient Muscle Fibers of MDX and ADR-MDX Mice is Reduced by Ion Channel Blockers. Journal of Physiology. vol. 515: pp. 859-868; entire document.

Wang, N et al. (1993) Mechanotransduction Across the Cell Surface and Through the Cytoskeleton. Science. vol. 260: pp. 1124-1127; entire document.

Wang, N et al. (2001) Mechanical Behavior in Living Cells Consistent with the Tensegrity Model. PNAS. vol. 98: pp. 7765-7770; entire document.

Wang, X et al. (2005) Uncontrolled Calcium Sparks Act as a Dystrophic Signal for Mammalian Skeletal Muscle. Nature Cell Biology. vol. 7: pp. 525-530; entire document.

(56) References Cited

OTHER PUBLICATIONS

Whitehead, NP et al. (2005) Muscle Damage in mdx (Dystrophic) Mice: The Role of Calcium and Reactive Oxygen Species. Proceedings of the Australian Physiological Society. vol. 36:pp. 111-117; entire document.
Whitehead, NP et al. (2006) Streptomycin Reduces Stretch-induced Membrane Permeability in Muscles from mdx Mice. Neuromuscular Disorders. vol. 16: pp. 845-854; entire document.
Whitehead, NP et al. (2010) Skeletal Muscle NADPH Oxidase is Increased and Triggers Stretch-Induced Damage in the mdx Mouse. PLoS One. vol. 5: pp. 1-10; entire document.
Wolff, AV et al. (2006) Passive Mechanical Properties of Maturing Extensor Digitorum Longus are not Affected by Lack of Dystrophin. Muscle and Nerve. vol. 34: pp. 304-312; entire document.
Yeung, EW et al. (2005) Effects of Stretch-activated Channel clockers on [Ca2+]i and Muscle Damage in the mdx Mouse. J. Physiol. vol. 562: pp. 367-380; entire document.
Young, MD et al. (2010) Gene Ontology Analysis for RNA-seq: Accounting for Selection Bias. Genome Biology. vol. 11: pp. 1-12; entire document.
Ziman, AP et al. (2010) Quantitative Measurement of Ca2+ in the Sarcoplasmic Reticulum Lumen of Mammalian Skeletal Muscle. Biophysical Journal. vol. 99: pp. 2705-2714; entire document.

\* cited by examiner

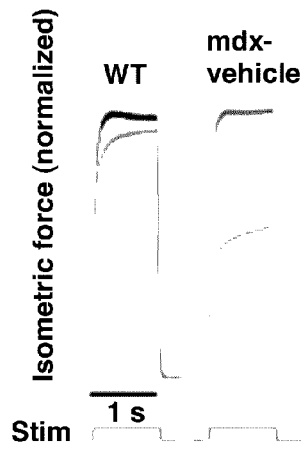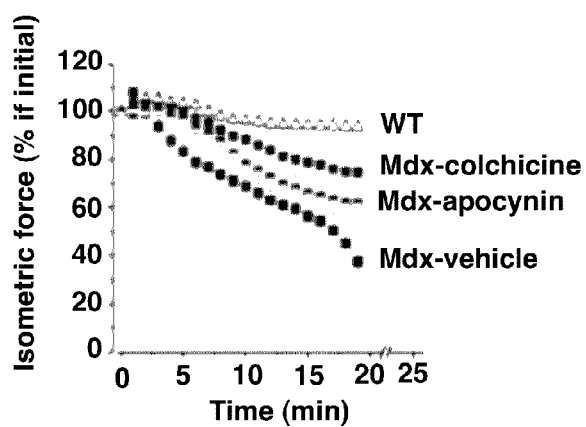
FIG. 6A FIG. 6B
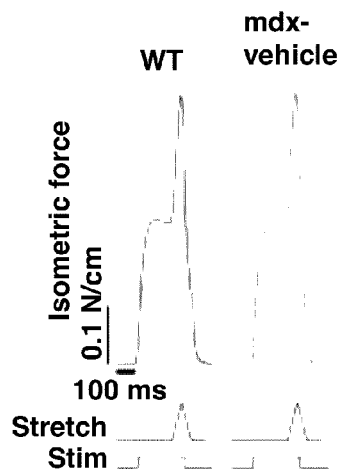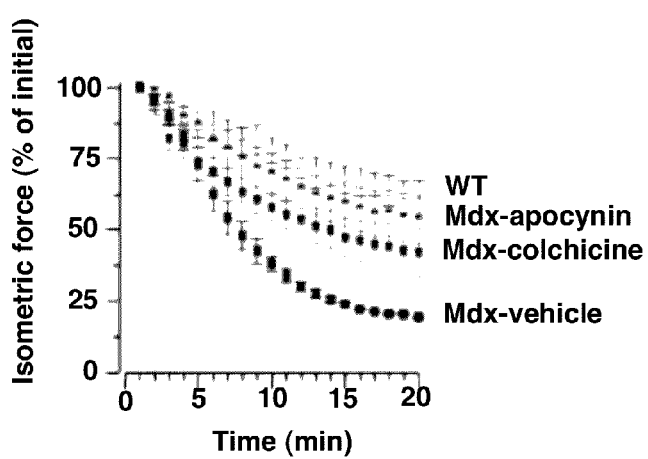
FIG. 6C FIG. 6D

TREATMENT OF MUSCULAR CONDITIONS AND MUSCULAR DYSTROPHIES

CROSS-REFERENCE TO RELATED APPLICATION

This application is a continuation-in-part patent application under 35 U.S.C. §120 of pending international patent application PCT/US2012/066177, filed Nov. 21, 2012, which claims priority claims benefit of priority under 35 U.S.C. §119(e) of provisional application U.S. Ser. No. 61/562,527, filed Nov. 22, 2011, now abandoned, the entirety of which is hereby incorporated by reference

STATEMENT OF FEDERALLY SPONSORED RESEARCH

This invention was made with government support under grant No. NR011968 awarded by the National Institutes of Health. The government has certain rights in the invention.

BACKGROUND OF THE INVENTION

1. Field of the Invention

The present invention relates to methods of treating neuromuscular degenerative disorders. More specifically, the present invention relates to methods of treating neuromuscular degenerative disorders by reducing the activation of NADPH Oxidase 2 (NOX2) either directly, or indirectly by means of the microtubule cytoskeleton.

2. Description of the Related Art

Duchenne Muscular Dystrophy (DMD) is a devastating, fatal, X-linked degenerative muscle disease that affects approximately 1 in 3,500 male births. While it is unequivocal that the absence of dystrophin is the molecular cause of DMD (1), the latency of disease presentation and spectrum of disease severity (2, 3) suggests that dystrophin alone does not explain the downstream muscle weakness and wasting. For example, several genetic factors have been identified that contribute to the onset and pathogenic progression of the disease (2, 3).

In human patients with DMD as well as in the most widely used murine model of DMD (mdx mouse), mechanical stress dependent dysregulation of $Ca^{2+}$ and reactive oxygen species (ROS) signaling has been identified as a critical factor in the dystrophic process (4-6). In response to membrane stressors (isometric and eccentric contraction, acute osmotic challenge, membrane deformation with suction etc.) mdx myofibers demonstrate an inability to maintain a low myoplasmic $[Ca^{2+}]$ compared to wild-type due in large part to increased sarcolemmal $Ca^{2+}$ influx through mechano-sensitive $Ca^{2+}$ channels (7-11). With the same perturbation, exuberant ROS production is also evident in mdx fibers leading to increased in $Ca^{2+}$ signaling dysfunction through oxidation of $Ca^{2+}$ channels (12, 13).

Membrane stress induces ROS production within the skeletal muscle transverse tubule (14) by activation of NADPH Oxidase 2 (NOX2) (15) through a mechano-transduction dependent pathway. In conjunction with NOX2 dependent ROS production in mdx muscle, ROS production has also been identified secondary to $Ca^{2+}$ entry into the mitochondria (16, 17). Acting independently or synergistically with $Ca^{2+}$ influx, mechanical stress induced ROS production has been proposed as a mechanism for the increase in susceptibility to muscle damage in mdx mice (4, 6, 18). Despite these recent advances in understanding the contribution of mechanical stress to muscle dysfunction in DMD, mechanistic detail for the mechano-transduction dependent activation of $Ca^{2+}$ and ROS pathways is limited.

The microtubule cytoskeleton resists mechanical perturbation in cells and in doing so act as a mechano-transducer (19-22). Dystrophin has been shown to be a microtubule associated protein (23). Nox2 has been shown to be activated by mechano-transduction (5, 14, 15) through Rac-1 as the mechano-sensitive element interacting with microtubules (24-26). In the heart, the microtubule network is critical for mechano-transduction dependent activation of $Ca^{2+}$ (27, 28) and NOX2 dependent ROS (27) signaling during diastolic stretch.

The prior art is deficient in means of treating muscular conditions, muscular dystrophies, as well as improving the function of normal muscle tissue. The present invention fulfills this longstanding need and desire in the art.

SUMMARY OF THE INVENTION

The present invention is directed to a method of improving muscular function in an individual. The method comprises the step of administering to the individual a pharmacologically effective amount of a compound that inhibits microtubule-dependent NADPH Oxidase 2 reactive oxygen species signaling production, wherein reduction in microtubule-dependent NADPH Oxidase 2 reactive oxygen species signaling production improves muscular function in said individual. The present invention is directed to a related method comprising the further step of administering a pharmacologically effective amount of a compound that blocks sarcolemmal $Ca^{2+}$ channel activation. The present invention is further directed to another related method comprising the further step of administering a pharmacologically effective amount of a compound that blocks renin-angiotensin signaling.

The present invention is further directed to a method of treating an individual having a muscular disorder. The method comprises the step of administering to the individual a therapeutically effective amount of a compound that inhibits microtubule-dependent NADPH Oxidase 2, thereby treating the muscular disorder in the individual. The present invention is directed to a related method comprising the further step of administering a pharmacologically effective amount of a compound that blocks sarcolemmal $Ca^{2+}$ channel activation. The present invention is directed to another related method comprising the further step of administering a pharmacologically effective amount of a compound that blocks renin-angiotensin signaling.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention are briefly summarized. The above may be better understood by reference to certain embodiments thereof which are illustrated in the appended drawings. These drawings form a part of the specification. It is to be noted; however, that the appended drawings illustrate preferred embodiments of the invention and therefore are not to be considered limiting in their scope.

FIG. 1A: Representative averaged data of adult (5-6 month) wild-type (n=5) and mdx (n=5) single FDB myofibers loaded with DCF and subjected to a 10% stretch. The DCF fluorescence profiles pre and post stretch were fit by linear least squares regression. The rates of DCF fluorescence pre- and post stretch were taken as the rate of ROS production. The DCF fluorescence change was normalized to the pre-stretch to allow comparison of the post stretch rates. FIG. 1B: NOX2 inhibition abrogates stretch induced ROS production in mdx. Fibers from wild-type (n=3 animals, 32 fibers) and mdx (n=3 animals, 23 fibers) were subjected to acute stretch with a scrambled peptide or with the NOX2 inhibitor gp91dsTAT. Mean values of DCF fluorescence, expressed as % change over pre-stretch rate, were significantly increased in mdx (*; p<0.05) compared to wild-type. In mdx fibers, stretch ROS production was inhibited by GP91dsTAT (#; p<0.05). FIG. 1C: The microtubule polymerization inhibitor colchicine also prevented the increase in X-ROS in mdx. FIG. 1D: Representative averaged data of 5-6 month adult wild-type and mdx single FDB myofibers loaded with fluo-4. FIG. 1E: Acute membrane stretch increases sarcolemmal calcium influx in mdx myofibers as measured by fluo4 fluorescence rate increase, and is prevented by GsMTx4 (n=2 animals, 10 fibers), a mechano-sensitive channel inhibitor as well as colchicine (n=3 animals, 12 fibers) and gp91dsTAT (n=2 animals, 8 fibers) (* denotes p<0.05 vs mdx). The rise in myoplasmic $Ca^{2+}$ with stretch was independent of sarcoplasmic reticulum release as ryanodine receptor inhibition did not block $Ca^{2+}$ influx (−0.005±0.046 pre-stretch rate compared to 0.751±0.296 stretch rate; p<0.01 paired t-Test). FIG. 1F: Western blot analysis of mdx tibialis anterior muscle displays a dramatic increase in abundance of the NOX2 subunits $gp91^{phox}$, $p67^{phox}$ and Rac-1. (T-Test; * p<0.05 vs wild-type).

FIGS. 3A-3B: Adult, but not young, mdx muscle have increased expression of the tubulin subunits α and β, as well as increased detyrosinated tubulin (glu-tubulin) when compared to age-matched wild-type muscle. (* p<0.05 vs young; n=6 animals per genotype per age). FIG. 3C: Immunohistochemistry of α-tubulin reveals an increased density of the microtubule network in mdx but not wild-type FDB. Inset panels reflect binarization of the region-of-interest denoted in the white-outlined center box. Microtubule density can be decreased with colchicine and increased with taxol. Scale bar is 20 μm. FIG. 3D: Quantification was performed on binary images of α-tubulin IHC. (n=2 animals, 12 fibers per genotype and condition)*p<0.05, ***p<0.001). FIG. 3E: Only adult mdx muscle displays X-ROS (n=2 animals, 14 fibers per genotype, *p<0.05 vs young; #p<0.05 vs wild-type) and FIG. 3F: dramatically increased calcium influx (n=2 animals, 10 fibers per genotype, *p<0.05 vs young; #p<0.05 vs wild-type). Data from adult wild-type and mdx is re-plotted from FIGS. 1B and 1D for comparison. FIG. 3G: Increasing microtubule density in young wild-type and mdx FDBs reveals X-ROS competent fibers. (n=2 animals, 11-14 fibers per genotype, *p<0.05, ***p<0.001)

FIGS. 5A-5B: Single fibers from dysferlin null mice exhibit significantly enhanced stretch induce ROS signaling. FIG. 5C: These muscles also demonstrate enhanced stretch induced calcium influx. FIG. 5D: Dysferlin null muscle exhibits enhanced protein expression of X-ROS proteins, i.e., tubulin isoforms and gp91. (p<0.05; ANOVA).

FIGS. 6A-6D show in vivo inhibition of X-ROS decreases contraction induced injury in mdx. Treatment of mdx mice in vivo was with either vehicle, colchicine or apocynin. Following treatment EDL muscle was assayed for susceptibility to either (FIGS. 6A-6B) in vitro isometric contraction induced injury or (FIGS. 6C-6D) in vivo eccentric contraction injury. (FIGS. 6A, 6C) Normalized isometric force transients of the initial (t=0; wild-type in black, mdx in red) and final (grey) contractions. (FIG. 6B) wild-type muscle (n=4) exhibited little force loss following this protocol while mdx (n=3) exhibited significant force deficits. Treatment with colchicine (n=4) or apocynin (n=4) resulted in a significant protection from force loss (p<0.05; ANOVA, NS, not significant vs wild-type). (FIG. 6D) wild-type muscle (n=3) displays a ~40% decrease in specific force generation following 20 eccentric contractions whereas force generation is almost completely wiped out in mdx. Treatment with colchicine (n=4) or apocynin (n=3) resulted in a significant protection from force loss (p<0.05; ANOVA, NS, not significant vs wild-type).

FIG. 9B shows that parthenolide treatment in vitro (10 uM; 2 hr) selectively reduced the population of Glu tubulin. (n=10; p<0.05; Students T-test). This result is in marked contract to colchicine treatment that ablated the majority of the cytoskeletal structure (FIG. 3C).

FIG. 10A) treatment with colchicine (10 uM; 2 hrs) or parthenolide (10 μM; 2 hrs) were equally effective at decreasing cytoskeletal stiffness as measured by axial compression by atomic force microscopy.stiffness (n=10 per condition; p<0.05; ANOVA). FIG. 10B shows that shortening velocity in unloaded muscle fibers in increased with parthenolide treatment consistent with a decrease in cytoskeletal stiffness. (n=12 per condition; p<0.05; ANOVA).

DETAILED DESCRIPTION OF THE INVENTION

Figure 1A:
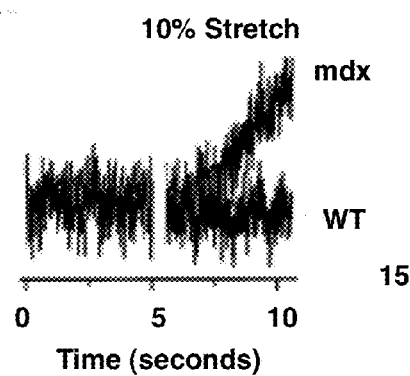
FIGS. 1A-1F show X-ROS signaling in dystrophic muscle fibers.

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, the term "individual" refers to the recipient of any compound described herein.

This invention provides new methods for improving both function and performance of normal muscle as well as treating neuromuscular degenerative disorders. The inventors have discovered contributing factors to the progression of neuromuscular degenerative disorders that were unknown. In DMD muscle, mechano-transduction (5-7) dependent activation of calcium ($Ca^{2+}$) and reactive oxygen species (ROS) signaling is associated with disease onset and pathogenic progression and is critical to enhanced contraction induced damage (8-13). Dystrophin is a microtubule associated protein whose absence results in a disorganized and densified microtubule cytoskeleton (14). The inventors have discovered that with physiologic stretch, microtubule-dependent NADPH Oxidase 2 (NOX2) ROS production (X-ROS) amplifies $Ca^{2+}$ influx through stretch activated channels (SACs).

Consistent with the importance of the microtubules to X-ROS, mdx muscle cells with low levels of microtubules (e.g., young or old treated with colchicine or nocodozole) have little X-ROS and $Ca^{2+}$ entry while those with high levels of microtubules, e.g., adult mdx, young WT treated with taxol, have exuberant X-ROS and $Ca^{2+}$ entry. As an empirical test, in vivo colchicine treatment ameliorated contraction-induced injury in adult mdx. Pertinent to this discovery, transcriptome analysis identified significant enrichment of X-ROS-related message in human DMD. Taken together, substantial evidence is provided showing that X-ROS is sufficient to account for pathogenic progression of mechano-transduction dependent $Ca^{2+}$ and ROS signaling in DMD and offers novel therapeutic targets for intervention.

As provided herein, a patient suffering from a neuromuscular degenerative disorder may be treated by administering a therapeutically effective amount of one or more compound that targets Reactive Oxygen Species Production (ROS) signaling components in muscle cells affected with a neuromuscular degenerative disorder. In some embodiments of the invention, the X-ROS signaling component is blocked by disrupting the microtubules of the cells. In other embodiments, the X-ROS signaling component is blocked by inhibiting NOX2. Further, as provided, more than one compound may be co-administered to treat a neuromuscular degenerative disorder by depolymerizing the diseased cells' microtubules and inhibiting the NOX2 at the same time. In addition, X-ROS signaling components are targeted with a therapeutically effective amount of a compound that blocks renin-angiotensin signaling. A compound that inhibits renin-angiotensin signaling may be co-administered with a microtubule inhibiting compound or a NOX2 inhibitor or a sarcolemmal calcium channel blocker.

While the working examples provided herein are directed towards DMD, one having ordinary skill in the art would recognize that these teachings would translate into other neuromuscular degenerative disorders. Neuromuscular degenerative disorders that may be treated using these methods include Duchenne Muscular Dystrophy (DMD), Becker's Muscular Dystrophy (BMD), Congenital Muscular Dystrophy (CMD), Limb-Girdle Muscular Dystrophy types 2A, 2B, 2D, 2E, or 2I. The methods taught herein may also be used to treat muscle diseases associated with mutations in the delta.-sarcoglycan gene, Ullrich congential muscular dystrophy (UCMD), congenital merosin-deficient 1A (MDC1A) muscular dystrophy, myositis, autophagic vacuolar myopathy, myopathies not associated with a specific protein deficiency, myotonic dystrophy type 1 (DM1), spinal muscular atrophy (SMA), critical care myopathy cases, Pompe disease, or sarcoidosis.

Representative compounds that may be used to depolymerize microtubules include but are not limited to colchicine, nocodozole, parthenolide, 2-phenyl-4-quinolone, polygamain, azaindole, vinca alkaloids, colcemid, analogs and derivative thereof. Representative compounds that may be used to inhibit NOX2 include fulvene, gp91ds, gp91ds comprising a peptide for enabling or enhancing cellular uptake, such as, but not limited to, a TAT peptide, apocynin, diphenylene iodonium, and each of their analogs or derivatives. Representative compounds that may be used to block sarcolemmal $Ca^{2+}$ channel activation include, but are not limited to, GsMTx4, streptomycin, poloxamer P188, ruthenium red, pyrazole-3, 3,5-bis(trifluoromethyl)pyrazole 2, N-(p-amylcinnamoyl)anthranilic acid, 4-Methyl-2-(1-piperidinyl)-quinoline, dantrolene sodium, and an SKF 96365 analog or derivative thereof. Representative compounds that may be used to block renin-angiotensin signaling include losartan, altace, lisinopril, enalapril, ramparil, zestril angiotensin converting enzyme inhibitors analogs and derivatives thereof, or their pharmaceutical salts. In consideration of the teachings of this application, one having ordinary skill in the art would likely recognize or be able to screen for other compounds that would be effective in targeting the X-ROS signaling component. These additional compounds should be considered part of this invention as they do not deviate from its spirit. Alternatively, the pharmaceutical salts of any compound may be utilized in the methods described herein.

The term "treatment" as used in this application may vary depending on the patient and the severity of the disorder. In some examples, the purpose of treatment will be to reduce fatigue in the patient. In other examples, the purpose of treatment will be to reduce muscle fatigue in the patient. Treatment may also comprise reducing stretch induced injury to muscles suffering from a neuromuscular degenerative disorder. Furthermore treatment may occur prior to, during or after onset of fatigue, muscle fatigue, damage or a muscle disorder and therefore encompasses administration to a healthy individual.

The dosage of each treatment depends on the type of compound being administered, whether the compound is used in an individual having a muscle disorder or in a healthy individual, the severity of the disorder or other muscle damage or fatigue, and the condition of the patient. After consideration of the teachings provided herein, one having ordinary skill in the art would be able to determine an effective dosage for a patient suffering from a neuromuscular degenerative disorder. As such, treatment intervals will depend on the particular dosage determined for the patient. Treatment may be administered multiple times per day, daily, or less frequently.

Thus, in one embodiment of the present invention, there is provided a method of improving muscular function in an individual, comprising the step of administering to said individual a pharmacologically effective amount of a compound that inhibits microtubule-dependent NADPH Oxidase 2 reactive oxygen species signaling production, wherein reduction in microtubule-dependent NADPH Oxidase 2 reactive oxygen species signaling production improves muscular function in the individual.

In one aspect of this embodiment, the compound depolymerizes microtubules. Representative examples of a compound that depolymerizes microtubules include, but are not limited to, colchicine, nocodozole, parthenolide, 2-phenyl-4-quinolone, polygamain, azaindole, vinca alkaloids, colcemid, analogs and derivative thereof, and pharmaceutical salts thereof. A person having ordinary skill in this art would readily be able to determine the appropriate dose of a compound that depolymerizes microtubules. Generally, compounds can be administered in a range from about 0.01 micrograms/kg to about 100 micrograms/kg. In a nonlimiting example, colchicine would likely be administered in an amount of from about 5 micrograms/kg to about 20 micrograms/kg of the individual's body weight.

In another aspect, the compound may be a NADPH Oxidase 2 inhibitor. Representative examples of a NADPH Oxidase 2 inhibitor include, but are not limited to, fulvene, apocynin, gp91ds comprising a TAT peptide or other peptide enabling cellular uptake thereof, diphenylene iodonium, pharmaceutical salts thereof and analogs and derivative thereof. A person having ordinary skill in this art would readily be able to determine the appropriate dose of a NADPH Oxidase 2 inhibitor useful in the methods of the present invention.

Further to this embodiment the method comprises administering a pharmacologically effective amount of a compound that blocks sarcolemmal $Ca^{2+}$ channel activation. Representative examples of a sarcolemmal $Ca^{2+}$ channel activation blocker include, but are not limited to, GsMTx4, streptomycin, poloxamer P188, ruthenium red, pyrazole-3, 3,5-bis(trifluoromethyl)pyrazole 2, N-(p-amylcinnamoyl)anthranilic acid, 4-Methyl-2-(1-piperidinyl)-quinoline, dantrolene sodium, and an SKF 96365 analog or derivative thereof, or a pharmaceutical salt thereof. A person having ordinary skill in this art would readily be able to determine the appropriate dose of a sarcolemmal $Ca^{2+}$ channel activation blocker useful in the methods of the present invention.

In another further embodiment, the method comprises administering a pharmacologically effective amount of a compound that blocks renin-angiotensin signaling. Representative examples of a renin-angiotensin signaling blocker include, but are not limited to, losartan, an analog or derivative thereof, or a pharmaceutical salt thereof. A person having ordinary skill in this art would readily be able to determine the appropriate dose of a compound that blocks renin-angiotensin signaling.

In another embodiment of the present invention, there is provided a method of treating an individual having a muscular disorder, comprising the step of a administering a therapeutically effective amount of a compound that inhibits microtubule-dependent NADPH Oxidase 2, thereby treating the muscular disorder in the individual. In one aspect of this method, the compound depolymerizes microtubules and is selected from the group consisting of colchicine, nocodozole, parthenolide, 2-phenyl-4-quinolone, polygamain, azaindole, analogs and derivative thereof, or their pharmaceutical salts. In another aspect of this method, the compound is a NADPH Oxidase 2 inhibitor selected from the group consisting of fulvene, apocynin, gp91ds comprising a TAT peptide or other peptide enabling cellular uptake thereof, diphenylene iodonium, pharmaceutical salts thereof and analogs and derivative thereof.

In a further embodiment, the method comprises administering a pharmacologically effective amount of a compound that blocks sarcolemmal $Ca^{2+}$ channel activation. A representative example of this compound is selected from the group consisting of GsMTx4, streptomycin, poloxamer P188, ruthenium red, pyrazole-3, 3,5-bis(trifluoromethyl) pyrazole 2, N-(p-amylcinnamoyl)anthranilic acid, 4-Methyl-2-(1-piperidinyl)-quinoline, dantrolene sodium, and an SKF 96365 analog or derivative thereof, or a pharmaceutical salt thereof In another further embodiment, the method comprises administering a pharmacologically effective amount of a compound that blocks renin-angiotensin signaling. As described above, the compound may be a renin-angiotensin signaling blocker such as losartan, an analog or a derivative thereof, or a pharmaceutical salt thereof.

In all embodiments of the methods of the present invention, representative examples of muscular disorders which may treated, include but are not limited to, Duchenne Muscular Dystrophy, Becker's Muscular Dystrophy, Congenital Muscular Dystrophy, Limb-Girdle Muscular Dystrophy, Limb-Girdle Muscular Dystrophy-2A, Limb-Girdle Muscular Dystrophy-2B, Limb-Girdle Muscular Dystrophy-2D, Limb-Girdle Muscular Dystrophy-2E, Limb-Girdle Muscular Dystrophy-2I, muscle diseases associated with mutations in the delta.-sarcoglycan gene, Ullrich congenital muscular dystrophy, congenital merosin-deficient 1A muscular dystrophy, myositis, autophagic vacuolar myopathy, myopathies not associated with a specific protein deficiency, myotonic dystrophy type 1, spinal muscular atrophy, critical care myopathy cases, Pompe disease, or sarcoidosis. Generally, treatment reduces muscle damage, activity-induced fatigue or muscle fatigue in said individual, thereby improving muscle function. Particularly, treatment reduces microtubule-dependent NADPH Oxidase 2 reactive oxygen species signaling production in the individual.

The following example(s) are given for the purpose of illustrating various embodiments of the invention and are not meant to limit the present invention in any fashion.

EXAMPLE 1

Materials and Methods
Reagents and Drugs

Reagents and drugs were purchased from Sigma-Aldrich (St. Louis, Mo.) unless otherwise noted. Taxol was purchased from Invitrogen (Carlsbad, Calif.). Lantrunculin A was purchased from Biomol (Farmingdale, N.Y.). gp91dstat peptide was purchased from Anaspec (Fremont, Calif., USA). Rac1 inhibitor was purchased from Calbiochem (San Diego, Calif., USA). Fulvene-5 was provided by Dr. Jack Arbiser.

Skeletal Muscle Isolation

After euthanasia by $CO_2$ inhalation, flexor digitorum brevis (FDB) muscle was harvested bilaterally and incubated in DMEM with 1 µl/ml gentamicin, and 0.4% collagenase A (Roche Applied Science, Indianapolis, Ind., USA) as described. Single intact myofibers were isolated by gentle trituration. The fibers were imaged and/or fixed for immunolabeling within an 8-h period (unless indicated), thus avoiding morphological changes that can occur in FDB fibers that are cultured for a prolonged period.

Myofiber Attachment and Stretch

All experiments were performed in custom rotating glass-bottom chamber (Four-hour Day Foundation, Towson, Md.) equipped with bath perfusion and mounted on BioRad Radiance fluorescent laser scanning confocal attached to an Olympus IX-70 inverted microscope (Olympus Corp., Centre Valley, Pa.). Cells were attached using micro-tweezers coated with the biological adhesive, MyoTak (Ionoptix, Milton, Mass.) and connected to a high-sensitivity force transducer (KG7) equipped with an anti-oscillation filter and a piezo-electric length controller (World Precision Instruments, Sarasota, Fla.). The force transducer and length controller were mounted on folded motorized micromanipulators (Siskiyou, Grants Pass, Oreg.) allowing to place the tweezers above the cell of interest. The rotating chamber, the tweezer-equipped force transducer and length controller and the micromanipulators formed the Muscle Stretch Tool (MUST).

Myofibers were attached at both ends by gently closing the MyoTak-coated tweezers without compressing the cell membrane and then lifting the cell from the bottom of the chamber. Cell sarcomere length was monitored using a High-speed Video Sarcomere Length camera (Aurora Scientific, Aurora, ON, CAN) and the voltage into the length controller was adjusted to produce a stretch equal to 10% of resting sarcomere length. The tension signal from the force transducer and positional output from the length controller were recorded at 1 kHz using a 600A data acquisition system from Aurora.

Reactive Oxygen Species (ROS) and Calcium Influx Measurements

ROS was measured using 6-carboxy-2",7"-dichlorodihydrofluorescein diacetate (DCFH-DA) (Invitrogen, Carlsbad, Calif.) in dimethyl sulfoxide (DMSO). FDB fibers were suspended in HEPES-buffered Ringer's solution containing (in mM): 140 NaCl, 4.0 KCl, 1.0 MgSO4, 5.0 NaHCO3, 10.0 glucose, 10.0 HEPES at pH 7.3 and incubated with Ringer's solution containing DCFH-DA (10 µM) for 30 minutes at room temperature. DCF-loaded cells were mounted on MUST and imaged using confocal line-scanning microscopy at 2 ms/line with very low laser intensity to prevent artifactual amplification of the signal due to light oxidation. DCF fluorescence signals were processed as described (16). The NOX2 specific inhibitor gp91dsTAT (2 µM), NOX inhibitor fulvene-5 (5 µM) and nitric oxide synthase inhibitor L-NAME (1 mM) was used to verify the source of ROS. Interrogation of cytoskeletal involvement in stretch dependent ROS or $Ca^{2+}$ influx was done with pharmacological methods. De-polymerization of the microtubule cytoskeleton was achieved with colchicine (10 µM), or nocodozole (10 µM) while depolymerization of the actin cytoskeleton was achieved with latrunculin A (10 µM). An increase in cytoskeletal network density was achieved with Taxol (10 µM).

Similar to DCF measurements, FDBs were suspended in Ringer's solution containing 5 µM fluo-4-AM (Invitrogen, Carlsbad, Ca) for 30 minutes at room temperature. Fluo-4-loaded cells were mounted on MUST and imaged using confocal line-scanning microscopy at 2 ms/line. Fluo-4 signal slopes before stretch and after were measured.

When the rate of DCF or $Ca^{2+}$ fluorescence increase is intrinsically low (as in young wild-type myofibers) or with inhibition (gp91dsTAT or GsmTx4 respectively), stretch resulted in a decrease in fluorescence rate. This result is consistent with both movement artifacts that is inherent with these studies at high spatial and time resolution and the redistribution of mobile dye molecules in the cytosol during stretch. While this negative deflection in DCF or Fluo-4 in low fluorescence conditions is an inherent aspect of this approach, this effect would only contribute to an underestimate of the actual stretch induced signals we see in this study and would not alter conclusions.

Western Blotting

Western blot analysis was performed as follows. In brief, 20 μg of clarified muscle extract was subjected to SDSPAGE, transferred to nitrocellulose membranes and washed/blocked in a 5% milk solution in PBS for 1 hour. The membrane was probed overnight with primary antibody at room temperature. The primary antibodies were anti-α-tubulin (DM1A, 1:1000; Sigma-Aldrich), anti-β-tubulin (AA12.1, 1:1000, DSHB), anti-Glu-tubulin (1:1000, Millipore, Temecula, Calif., USA), anti-gp91$^{phox}$ and anti-p67$^{phox}$ (1:1000, BD Transduction Laboratories, Lexington, Ky.), anti-rac1 (1:1000, Millipore) and anti-GAPDH (1:4000, Millipore). Membranes were washed two times for 10 minutes in 5% milk solution at room temperature, incubated with appropriate secondary antibody (1:10,000) for 1 hour at room temperature, and the membranes were washed in a 0.5% Tween solution in PBS two times for 10 minutes. Membranes were then exposed to enhanced chemiluminescence with SuperSignal West Pico Chemiluminescent Substrate (Pierce, Rockford, Ill.) to develop immunoblots. Blots were imaged and quantified with an imaging system (SYN-GENE, G:Box; GeneTools software). The GAPDH density signal served as the loading control.

Immunohistochemistry

Tibialis anterior muscles were flash frozen (isopentane ~−40° C.) and serially sectioned (16 μm) perpendicular to the fiber axis at the muscle mid-belly. Muscle sections were fixed in paraformaldehyde and stained with antibodies for macrophages (eBioscience, anti-F4/80), CD4+ (BD Biosciences Clone H129.19) and CD8a+ (BD Biosciences Clone 53-6.7) T-cells. Antibody labeling was visualized with 3,3'-diaminobenzidine peroxidase kit (Vector labs, USA). The sections were then digitally imaged (Olympus DP70 CCD camera) on an upright microscope (Olympus BX-50) with a 20× PlanF objective. Immune cells were identified and counted visually by a blind rater. Due to the extremely low occurrence of T cells in these sections, only data on macrophage infiltration (F480 reactivity) was quantified and presented.

Fluorescence Labeling and Quantification of α-Tubulin

Isolated intact FBDs were plated on ECM gel from Engelbreth-Holm-Swarm murine sarcoma coated imaging dishes (MatTek, Ashland, Mass.). Following treatment, plated myofibers were fixed with 2% paraformaldehyde, permeabilized with 0.1% Triton X-100 in phosphate buffered saline (PBS), blocked in 8% bovine serum albumin in PBS, and then labeled overnight with an antibody to α-tubulin conjugated to Alexa Fluor 488 (anti-mouse; Invitrogen, Carlsbad, Calif., USA). Digital images were obtained with a BioRad Radiance fluorescent laser scanning confocal attached to an Olympus IX-70 inverted microscope. Laser intensity was adjusted on a sample-to-sample basis to maximize amount of microtubules that are visualized. A 35-image Z-stack was taken at 0.5 μm interval and the most representative 9 frames were stacked together using ImageJ (NIH, USA) to form a composite image. Quantification was performed on the binary image representation of the 9-image stack. Background was subtracted uniformly and image was transformed into a binary using ImageJ unbiased binary function. A uniform region of interest was selected and mean intensity measured.

In Vitro Isometric Contraction-Induced Injury

Following $CO_2$ asphyxiation and cervical dislocation, single EDL muscles were surgically excised with ligatures at each tendon (5-0 silk suture) and mounted in an in vitro bath between a fixed post and force transducer (Aurora 300B-LR) operated in isometric mode. The muscle was maintained in physiological saline solution and maintained at 30° C. under aeration with 95 $O_2$/5 $CO_2$ (%) throughout the experiment. Resting tension, muscle length and stimulation current were iteratively adjusted for each muscle to obtain optimal twitch force. During a 5 minute equilibration, single twitches were elicited at every 30 seconds with electrical pulses (0.5 msec) through platinum electrodes running parallel to the muscle. The injury protocol used to induce a force deficit (39) consisted of 20 maximum isometric contractions (1 sec at 100 Hz) separated by 1 minute. The absolute isometric force of each muscle during the contraction protocol was normalized to the maximum isometric force ($P_o$) produced by the muscle during the 20-contraction protocol. The % of force decline between the $1^{st}$ and $20^{th}$ contraction was taken as the extent of contraction induced injury.

In Vivo Eccentric Contraction-Induced Injury

Eccentric injury of the gastrocnemius muscle was conducted in vivo using a 305B muscle lever system (Aurora Scientific Inc.) as described but with minor modification. Anaesthetized mice (isoflurane) were placed on a thermostatically controlled table, the knee was fixed with a pin and the foot was firmly fixed to a footplate on the motor shaft. Contraction was elicited by percutaneous electrical stimulation of the sciatic nerve. Optimal isometric tetanic torque was determined with increasing current with a minimum of 30 s between each contraction to avoid fatigue. Eccentric contractions at maximal isometric torque (0.2 ms pulse train at 100 Hz) were assayed for the resistance to muscle damage.

Eccentric contractions were achieved by lengthening the muscle during maximal contraction. This was achieved by translating the footplate 30° at a velocity of 40 mm/s following the first 200 msec of the isometric contraction. This protocol consisted of 20 eccentric contractions with 1 minute pauses in between. The decrease in the peak isometric force prior to the eccentric phase was taken as an indication for muscle damage. To test the role of X-ROS in the functional status of mdx muscle, adult mdx mice were treated with either colchicine (1 mg/kg IP; 4 hours) or apocynin (3 mg/kg IP; 3 days) in vivo to reduce X-ROS signaling followed by a contraction protocol to produce mechanical stress.

Microarray and RNA Sequencing

The subjects in this study were obtained from referrals for molecular diagnostic services to be performed at the Hoffman laboratory at Children's National Medical Center in Washington, D.C. The samples were processed uniformly and a standard diagnostic set of tests was performed including biochemical and histological methods. These assays included dystrophin immunostaining and immunoblotting and hematoxylin and eosin histological stains, which were performed according to standard methods. RNA or frozen biopsy samples from control subjects (n=6) with normal muscle pathology and DMD subjects (n=6) were sequenced. For microarray studies, RNA extracted from six control subjects and 17 DMD subjects was profiled. Total RNA was extracted from frozen muscle biopsies using standard Trizol methods (Invitrogen, Carlsbad, Calif., USA). RNA quality and concentration were assayed using a Nanodrop spectrophotometer.

Microarray expression profiling to validate the sequencing data was performed according to the manufacturer protocols (Affymetrix, Santa Clara, Calif.). Briefly, total RNA was used to prepare biotinylated cRNA, followed by fragmentation and hybridization to Affymetrix arrays (Genechip HG U133Plus2; Affymetrix, Santa Clara, Calif.). The arrays were incubated for approximately 16 hours, washed, stained, and scanned per Affymetrix. Differential gene expression through microarray was then performed. . cel files were utilized to generate from Affymetrix profiling process for analysis. Arrays were normalized by GCRMA method implemented in gcrma R package. Differential expression analysis was performed using limma R package. First a linear model was fitted to expression data for each gene. Empirical Bayes method was then used to assess differential expression between two conditions. A cutoff of FDR less than 0.01 and 2 fold change was used to select significant probes.

RNA sequencing was conducted on the Illumina HiSeq System (Illumina, Inc., San Diego, Calif.) to obtain 100 base pair (bp) paired-end reads. We obtained an average of 148.3 million reads per sample with an average of 90% of the reads aligning to exonic regions in the genome. These reads were mapped to the GRCh37/hg19 build of the human genome using the short-read aligner TopHat (version 1.2.0). The segment-length, max-multihits, max_cov_juncs, max_seg_juncs, and parameters were optimized in TopHat to generate contiguous as well as spliced alignments. The alignments were merged to form complete alignments to the genome. These alignments served as the basis of further downstream analysis including differential gene expression analysis and pathway analysis. Differential gene expression by RNA Seq was then performed. The number of reads mapped on each gene were counted by HTSeq program against gene annotation file for GRCh37/hg19 build from Ensembl. Read counts were used to measure gene expression levels.

Data normalization and differential expression analysis were performed using the methods implemented in the R package DESeq 1.2. Briefly, DESeq normalizes read counts for sequencing depth and distortion caused by highly differentially expressed genes. A negative binomial (NB) model is then used to test the significance of differential expression between two conditions. The criteria used to select significant genes include a FDR (False Discovery Rate) cutoff of less than 0.05, more than a two-fold change in gene expression between conditions, and normalized read count of 10 reads per gene in at least one condition.

Gene ontology (GO) analysis on selected significant genes was performed using R package goseq. Gene length bias existed in RNA-seq has been taken into account when the enrichment of GO category was computed. A FDR cutoff of less than 0.05 was used to select significantly enriched GO categories. This information was used to examine X-ROS signaling components. Interrogating the data for these genes, we constructed a pathway using Ariadne Pathway Studio (Ariadne Genomics [Elsevier], Rockville, Md., USA).

Statistical Analysis

Data was analyzed for normality and equal variance. Unless stated otherwise, parametric data were analyzed by one-way or two way analysis of variance (ANOVA) followed by Holm-Sidak for multiple comparisons. When assumptions for normality and variance were not met, data were analyzed by one way or two way ANOVA on Ranks with a Dunn's post-test for multiple comparisons. All analyses were conducted in SigmaPlot 11.0 (Systat Software inc. San Jose, Calif.). Data are presented as means±SEM, with significance set at P<0.05.

EXAMPLE 2

Results

Recently, the inventors developed a technique termed "MuST" (Muscle Stretch Tool), technology enabling establishment of a minimal model of stretch activated mechanotransduction in skeletal muscle that avoids potential confounders of membrane damaging force (eccentric injury), exercise, or non-physiologic stress such as osmotic shock. Using MUST, a brief (5 seconds) small (~10% sarcomere length) axial stretch was imposed on intact flexor digitorum brevis muscle fibers. In wild-type (WT) myofibers loaded with a fluorescent ROS probe (6-carboxy-DCF-AM), axial stretch elicited a small non-significant (7%) increase in ROS production. In contrast, stretch elicited a dramatic, transient increase in ROS production in adult mdx myofibers (a murine model of DMD) (FIG. 1A).

Figure 1B:
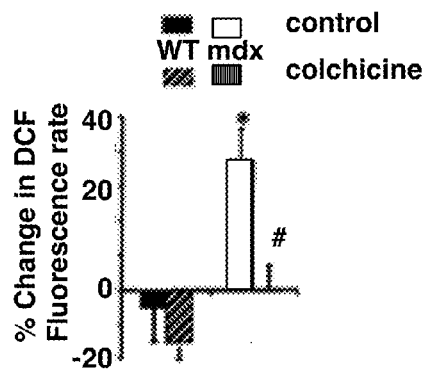
Figure 2:
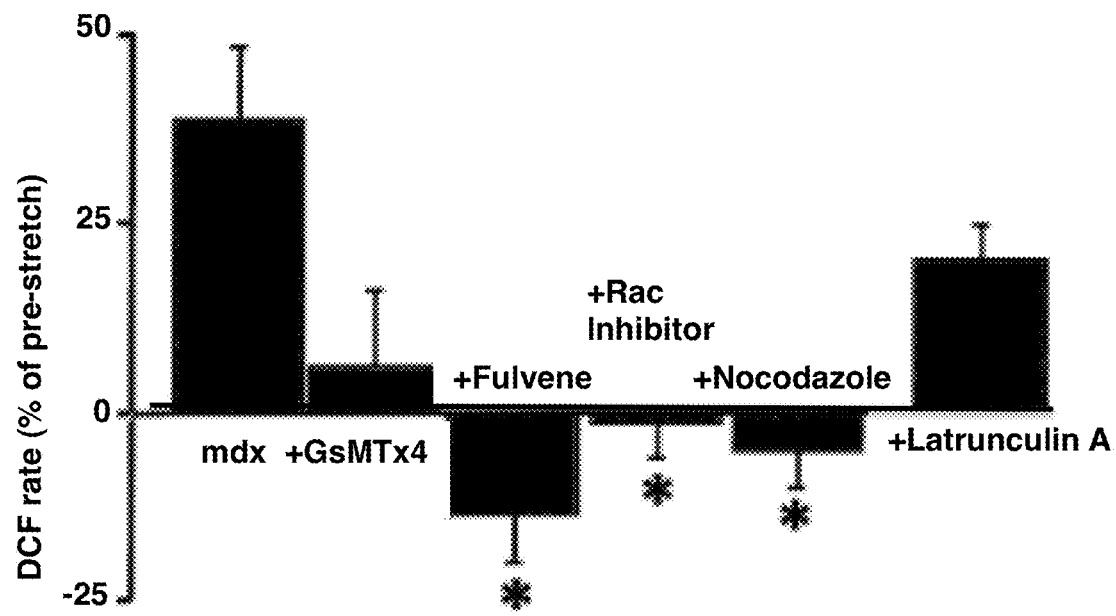
FIG. 2 demonstrates that the inhibition of NOX2 with Fulvene 5 or RAC, microtubule associated protein that activates NOX2 with stretch, inhibition is effective at abrogating X-ROS in mdx myofibers. Importantly, inhibition of microtubule structure with nocodozole was equally effective as colchicine while disrupting the actin cytoskeleton (latrunuculin A) has no significant effect.

Cytoskeletal networks propagate mechanical signals throughout muscle cells (29). Dystrophin is a microtubule associated protein whose absence results in a disorganized and densified microtubule cytoskeleton (23). In the adult mdx muscle, pharmacologic de-polymerization of the microtubule cytoskeleton (10 µM colchicine, FIG. 1B; or 10 µM nocodozole, FIG. 2) or inhibition of the Rac-1 GTPase (FIG. 2) ameliorated the stretch-induced ROS production while de-polymerization of the actin cytoskeleton (10 µM latrunculin A, FIG. 2) or inhibition of nitric oxide synthase (1 mM L-NAME; not shown) had no effect.

The reduced-form nicotinamide adenine dinucleotide phosphate (NADPH) oxidase 2 (NOX2) is activated by mechanotransduction (27) and is critical in the pathology of DMD (5). Inhibition of NOX2 with the specific inhibitor gp91dsTAT (30) (FIG. 1C) or fulvene-5 (FIG. 2) (31) verified NOX2 as the source of the stretch dependent ROS in the adult mdx muscle fiber. Thus, in adult mdx muscle, the microtubule network is responsible for the transmission of mechanotransduction signals through NOX2 to generate ROS, a process termed X-ROS (27).

Figure 1D:
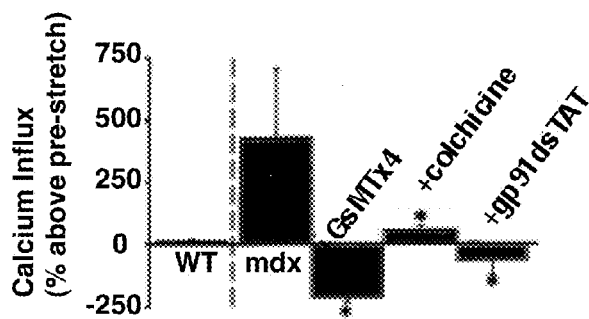
Figure 1E:
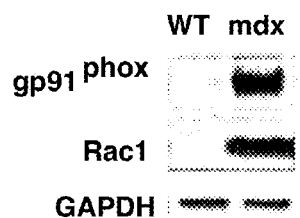
Figure 1C:
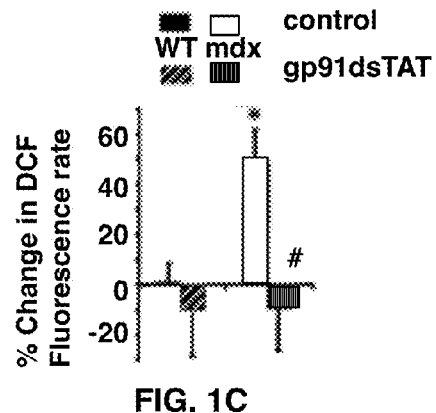

Dysregulated $Ca^{2+}$ signaling is a hallmark of the dystrophic process and a brief stretch significantly increased the rate of cytosolic $Ca^{2+}$ accumulation in adult mdx muscle fibers (~5 fold) when compared to wild-type muscle fibers (~0.2 fold; FIG. 1D). Consistent with use of axial stretch as a physiologic perturbation, no $Ca^{2+}$ sparks accompanied the rise in cytosolic $[Ca^{2+}]$ observed in mdx muscle unlike those reported with osmotic shock (32). The rise in myoplasmic $Ca^{2+}$ with stretch was independent of sarcoplasmic reticulum release as ryanodine receptor inhibition did not block $Ca^{2+}$ influx (−0.005±0.046 pre-stretch rate compared to 0.751±0.296 stretch rate; p<0.01 paired t-Test). Further, the stretch dependent rise in $[Ca^{2+}]$ is the due to sarcolemmal $Ca^{2+}$ influx into the myocyte through enhanced activation of stretch activated $Ca^{2+}$ channels (SACs) as it was ablated by the SAC blocker GsMTx4 (2.5 µM) (33, 34) (FIG. 1E). Stretch dependent $Ca^{2+}$ influx was ablated by the microtubule depolymerizing agent colchicine and the NOX2 inhibitor gp91dsTAT, revealing that X-ROS signaling is responsible for the enhanced mechano-transduction dependent $Ca^{2+}$ influx in mdx muscle fibers (FIG. 1E).

Figure 1F:
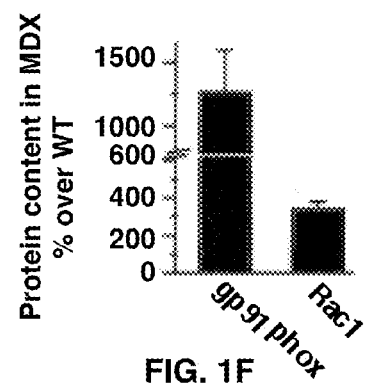
Figure 3A:
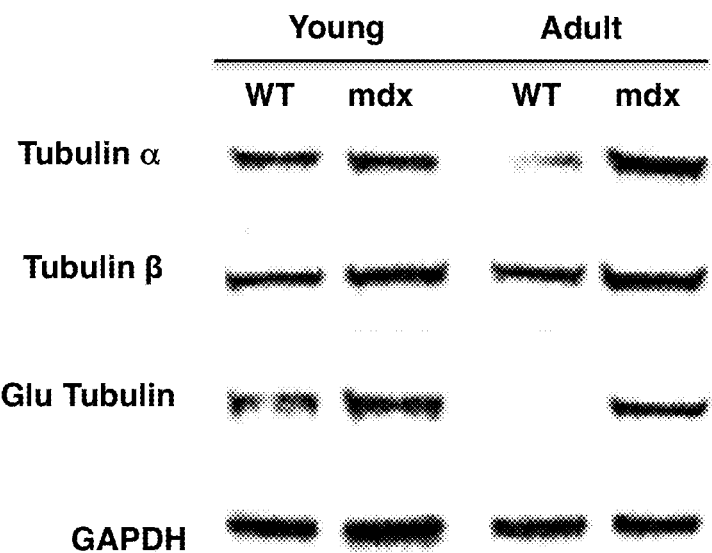
FIGS. 3A-3G show that only adult dystrophic muscle display up-regulation of the microtubule network, an upstream modulator of X-ROS.
Figure 3B:
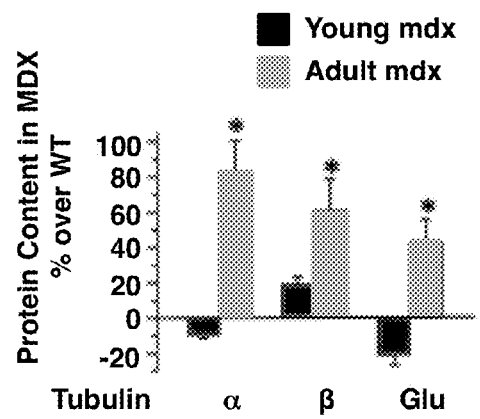
Figure 3C:
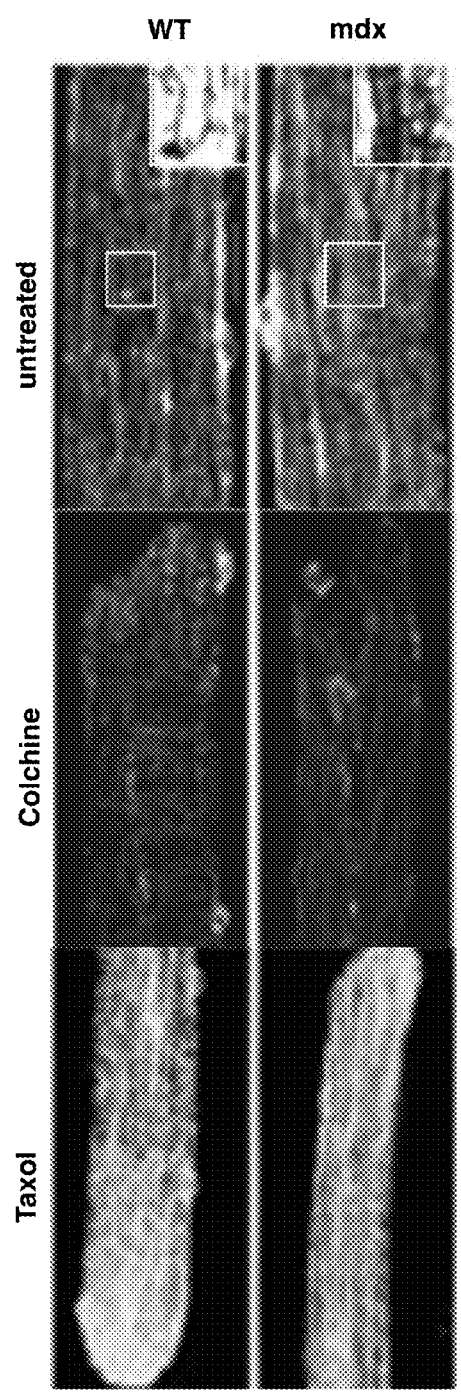
Figure 3D:
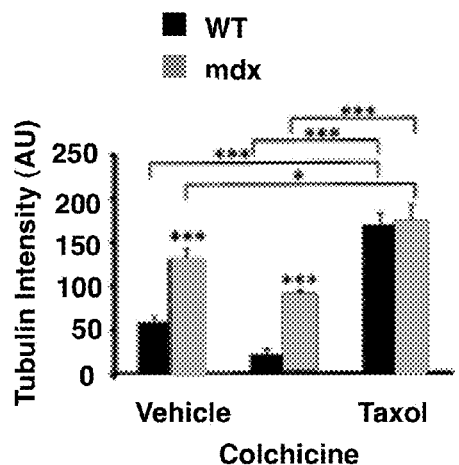

Insight into the increased X-ROS in adult mdx muscle fibers comes from Western blot that reveals a significant increase in NOX2's catalytic ($gp91^{phox}$), regulatory ($p67^{phox}$) and microtubule associated subunits (Rac-1) (FIG. 1F). These increases are independent of immune cell infiltration as the adult mdx muscle displays lower immune cell counts then young mdx muscle which is consistent with other reports (35). Furthermore, microtubule protein subunit abundance (FIGS. 3A-3B) and network density (FIGS. 3C-3D), all essential components of X-ROS, are also increased. In DMD, enhanced mechanotransduction activated signaling pathways increase the susceptibility to muscle damage (5). Furthermore, reports suggest a temporal progression in the susceptibility to stretch induced damage of mdx muscle (37, 38). Muscle examined from young (~6-8 weeks) mdx showed that the microtubule subunit content (FIG. 3A) as well as membrane stiffness was not different between young wild-type, young mdx and adult wild-type muscle fibers when compared to adult mdx. The amount of gp91$^{phox}$ and Rac-1 was below amounts necessary for reliable detection in the young of each genotype.

Figure 3E:
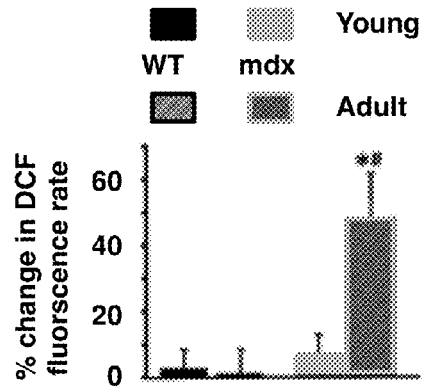
Figure 3F:
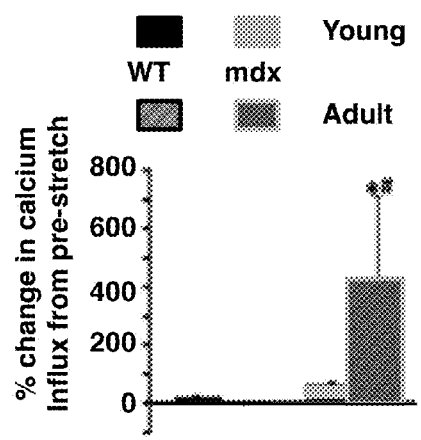
Figure 3G:
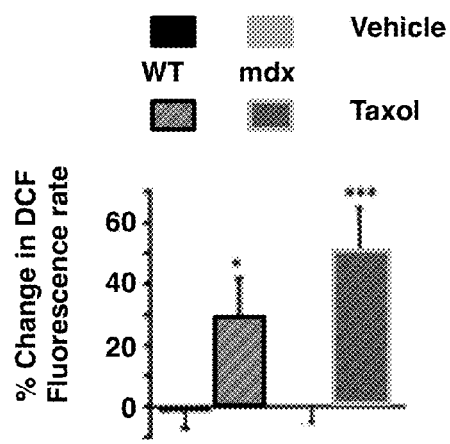

As an empirical test for the temporal progression of X-ROS signaling in mdx muscle, it was demonstrated that X-ROS, as well as its downstream activation of stretch dependent Ca$^{2+}$ influx, was significantly increased only in adult mdx muscle fibers, correlating with the increase in X-ROS components in the adult compared to young mdx fibers (FIGS. 3E-3F). As a direct test of the importance of the microtubule network in X-ROS, young wild-type or young mdx muscle fibers were made X-ROS competent by experimentally increasing the density of the microtubule cytoskeleton (taxol, FIG. 3G).

Figure 4A:
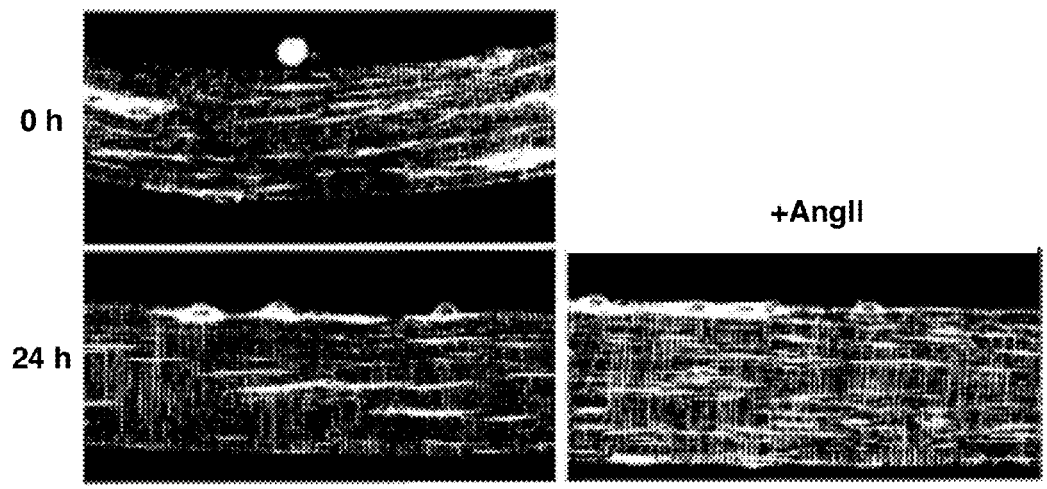
FIGS. 4A-4B shows Angiotensin II treatment increases microtubule density in isolated FDB myofibers over 24 hrs as demonstrated via fluorescent staining (FIG. 4A) and an increase in fluorescence emission intensity (FIG. 4B).
Figure 4B:
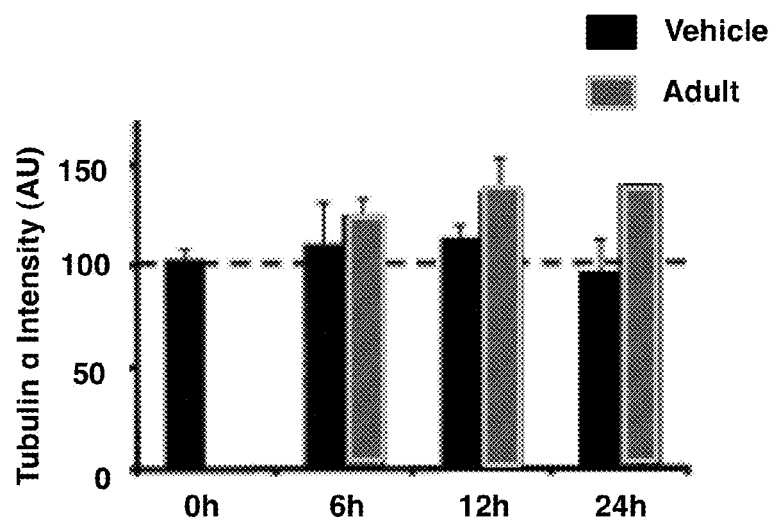

A complete transcriptome analysis was utilized to address X-ROS signaling in human DMD. This demonstrated the significant enrichment of, for example, NOX2 subunits and tubulin isoforms. The proximate location of the TGF and angiotensin signaling pathways are relevant, as it was reported that both TGF receptors and the muscular renin-angiotensin are activated in human DMD muscle (22). Moreover, inhibition of these pathways has been shown to be beneficial in both human DMD (23) and in mdx (24-25). Predictably, angiostensin II increased microtubule subunit content in C2C12 myotubes and acute administration of angiotensin II densified the microtubule network in isolated FDBs (FIGS. 4A-4B).

Figure 5A:
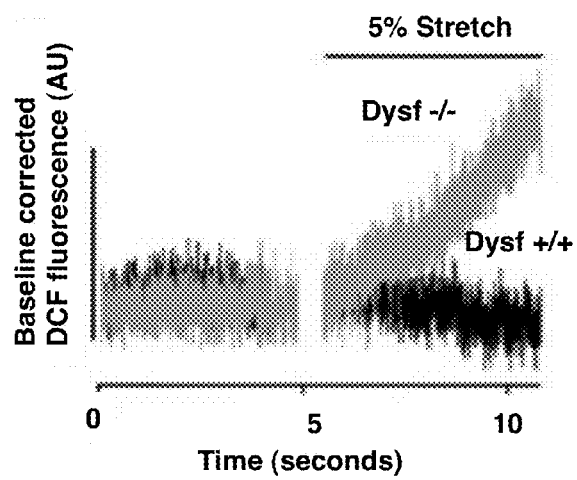
FIGS. 5A-5D show that dysferlin null mice in a murine model of limb girdle myopathy type IIb exhibits X-ROS signaling.
Figure 5B:
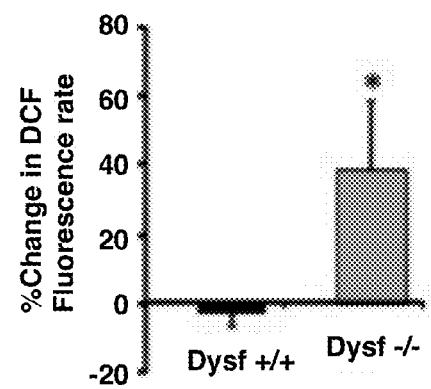
Figure 5C:
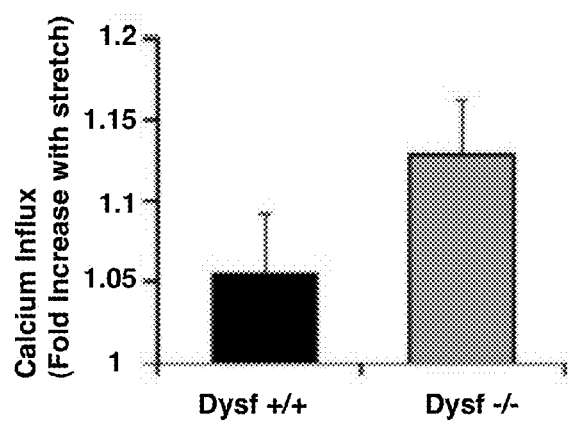
Figure 5D:
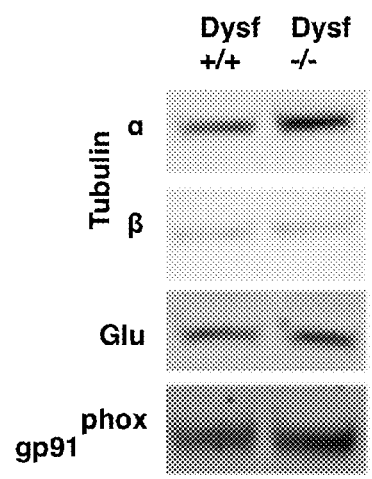

In a murine model of limb girdle myopathy type IIb, single fibers from dysferlin null mice demonstrate a significant enhancement of stretch induced ROS signaling (FIGS. 5A-5B) and calcium influx (FIG. 5C). It is further demonstrated that muscle in dysferlin null mice show increased protein expression of X-ROS proteins, such as, tubulin isoforms and gp91 (FIG. 5D).

Figure 7:
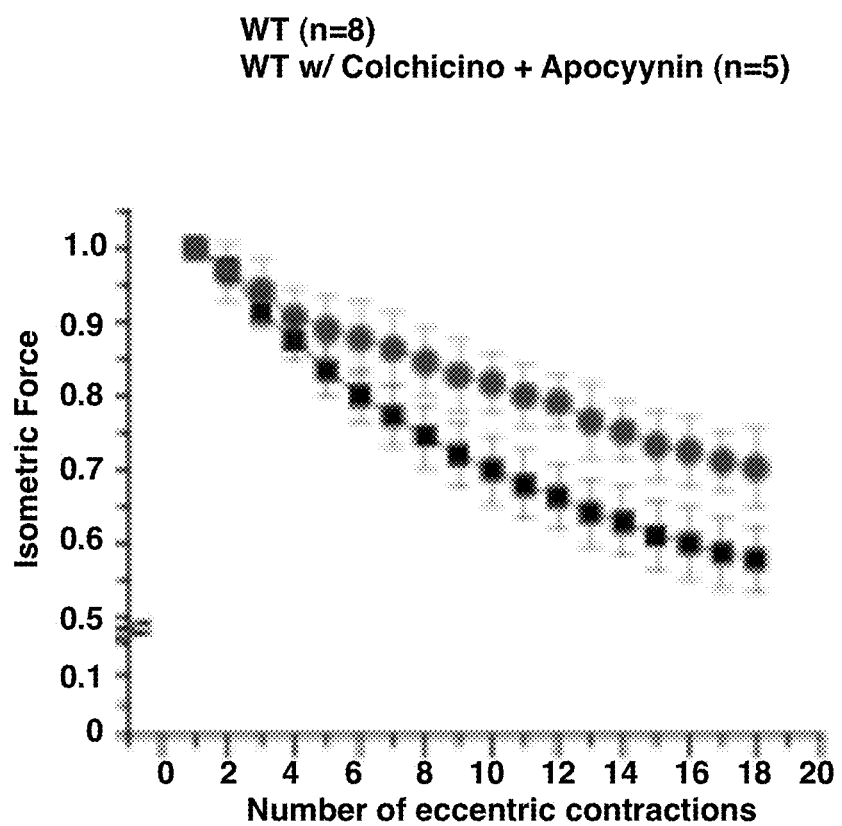
FIG. 7 shows in vivo inhibition of X-ROS decreases contraction-induced injury in wild-type (WT) mice. WT mice were treated in vivo with either vehicle, or a combination of colchicine and apocynin. Following treatment, the gastrocnemius muscle was assayed for susceptibility to in vivo eccentric contraction injury. Wild-type muscle (n=8) displays a ~40% decrease in specific force generation following 18 eccentric contractions whereas the force drop force was significantly less in the treated mice (n=5). (p<0.05; ANOVA).

In DMD skeletal muscle, mechanical stress activates Ca$^{2+}$ and ROS signaling pathways that contribute to muscle injury (4-6). To test the role of X-ROS in the functional status of mdx muscle, adult mdx mice were treated with either colchicine, or parthenolide (LC-1) or apocynin in vivo to reduce X-ROS signaling followed by a contraction protocol to produce mechanical stress. An established isometric contraction protocol in vitro was used to provide a moderate stress challenge that resulted in no force loss in wild-type yet significant deficits in mdx (39). Treatment with either colchicine or apocynin or LC-1 in vivo significantly decreased the isometric contraction induced force loss in the mdx (FIGS. 6A-6B). In a second set of experiments eccentric contractions in vivo were used (40). As with the isometric contractions, either treatment significantly reduced contraction induced force loss (FIGS. 6C-6D). Treatment in vivo of wild type mice with either colchicines or apocynin significantly decreased the eccentric contraction induced force loss (FIG. 7).

Figure 8:
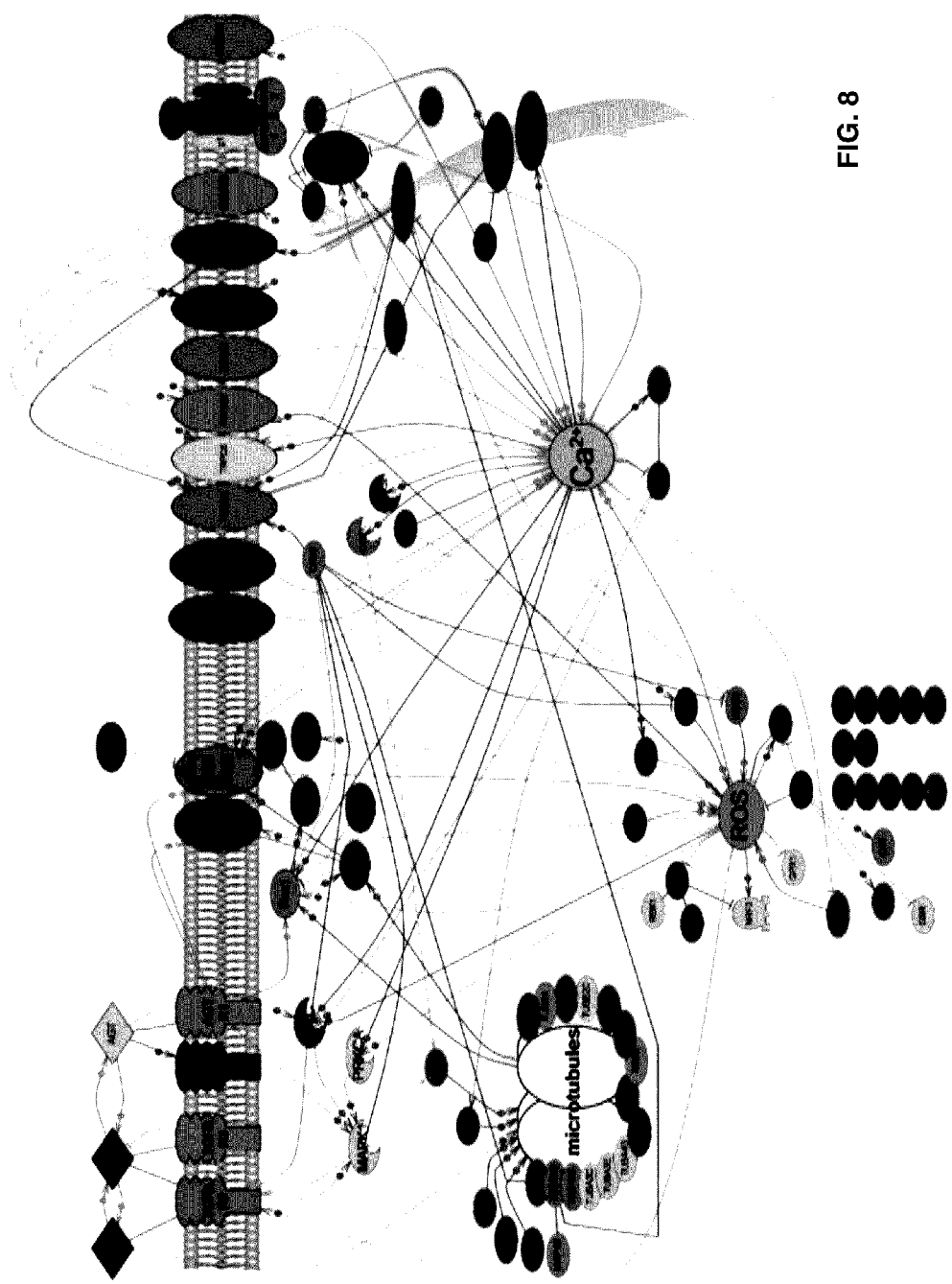
FIG. 8 shows a transcriptome analysis of DMD clinical biopsy samples supports X-ROS signaling mechanism. Genes in red are significantly up-regulated in DMD muscle and those in blue are significantly down-regulated in DMD muscle. Arrows represent direct positive regulation. Blunt arrows represent negative regulation. AGT, angiotensin II; AGTR, angiotensin II receptor; CALM, calmodulin; CASQ, calsequestrin; CAT, catalase; CAV3, caveolin 3; CUL3, cullin 3; DHPR, dihydropyridine receptor; GLRX, glutaredoxin; GSR, glutathione-S-reductase; GST, glutathione-S-transferase; JCTN, junction; MAO, monoamine oxidase; MAP, microtubule associated protein; NOS, nitric oxide synthase; PLN, phospholamban; PRDX, peroxiredoxin; PRKCA, protein kinase Cα; SERCA, sarco/endoplasmic reticulum Calcium ATPase; SOD, superoxide dismutase; STMN1, stathmin 1; TGFBR, TGFβ Receptor; TRDN, triadin; TRP, transient receptor potential; TUBA, tubulin α; TUBB, tubulin β; TXN, thioredoxin; TXNRD, thioredoxin reductase. The legend inset provides information regarding classification and how the genes regulate other genes. These results, in clinical patient samples, suggest that the X-ROS signaling pathway is operant in the human DMD muscle.

Having established X-ROS as a therapeutic target in the mdx mouse, X-ROS signaling in human DMD was addressed. A complete transcriptome analysis of clinical diagnostic muscle samples was conducted (FIG. 8). As the X-ROS signaling pathway is not a canonical pathway, a pathway de novo was constructed (not shown). There was a significant enrichment of X-ROS related transcripts in the human DMD muscle including every NOX2 subunit, 9 different tubulin isoforms, as well as several SAC candidate genes. In addition, there was differential enrichment of transcripts for canonical Ca$^{2+}$ pathways, i.e., EC coupling related proteins such as ryanodine receptor, DHPR subunits and SERCA were down regulated, while several TRP channels, ORAI3 and the sodium-calcium exchanger were upregulated. Furthermore, several antioxidant defense proteins, such as catalase, superoxide dismutase and thioredoxin were also down regulated. All of these changes are consistent with a probable enhancement of X-ROS and sarcolemmal Ca$^{2+}$ influx in human DMD muscle and support X-ROS as a potential therapeutic target in patients.

Figure 9A:
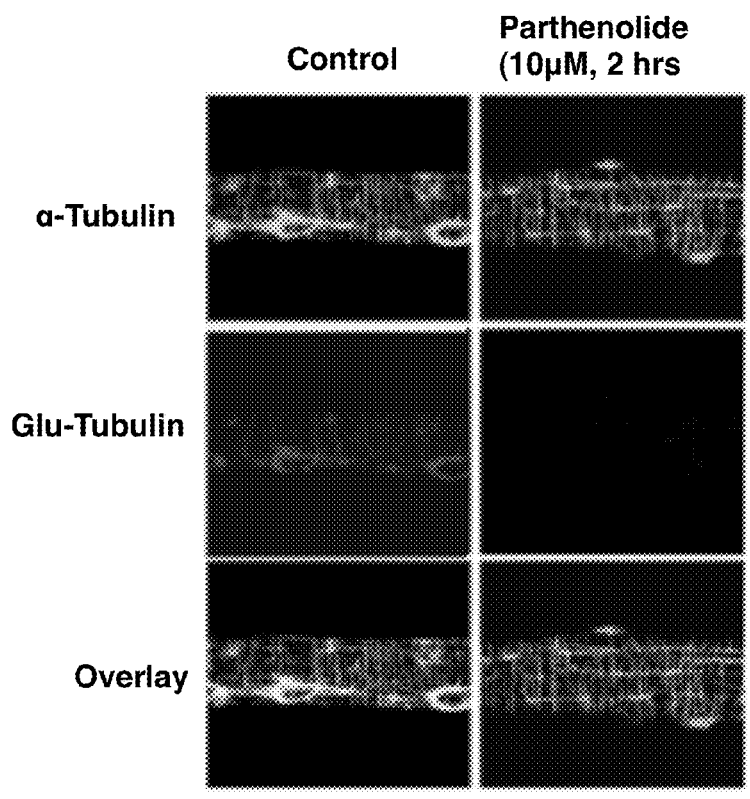
FIGS. 9A-9B show that in wild-type (non-diseased) skeletal muscle, a significant portion of the α-tubulin network (green pseudocolor secondary stain) is comprised of post-translational modified, detyrosinated, α-tubulin (also known as Glu tubulin; red pseudocolor secondary stain) (FIG. 9A). As indicated previously, an increase in Glu tubulin was seen in mdx muscle (FIGS. 3A-3B) and dysferlin deficient muscle (FIG. 5D).
Figure 9B:
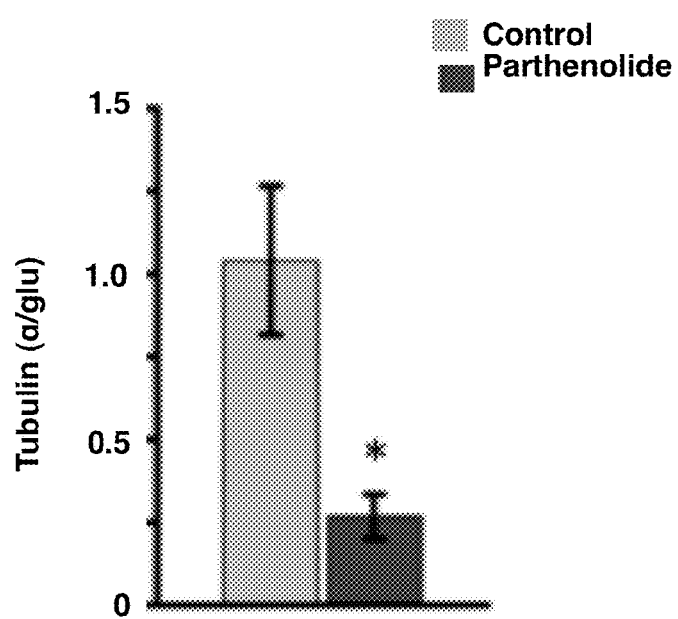
Figure 10A:
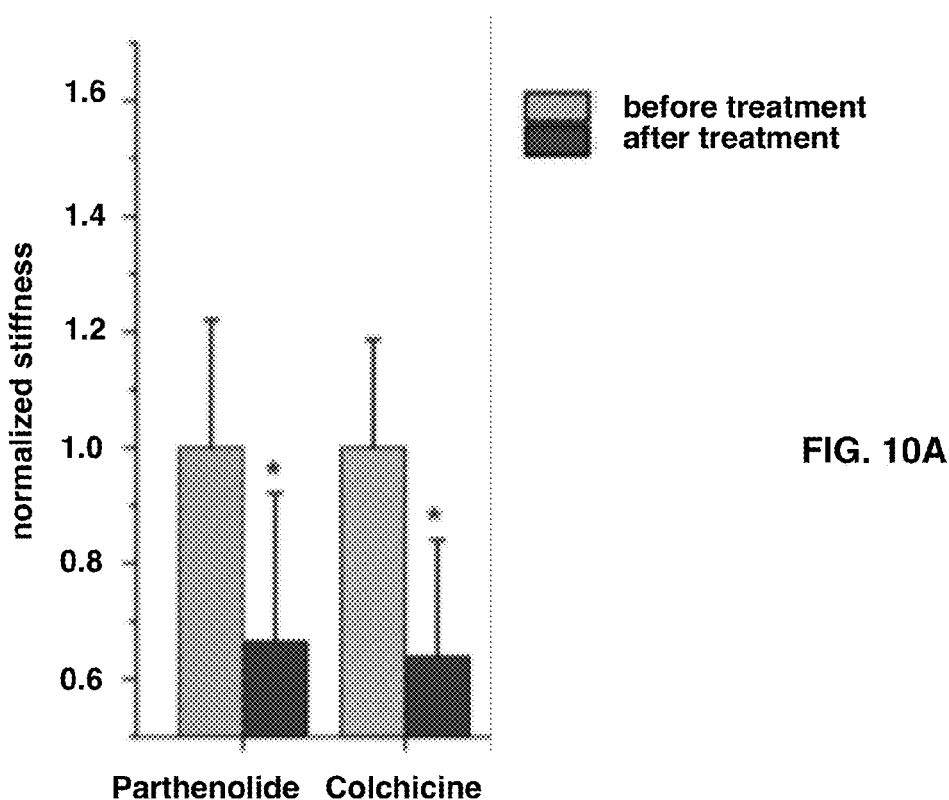
FIGS. 10A-10B show that the parthenolide targeted decrease in Glu tubulin improved the mechanical properties of the muscle fiber. In wild-type (non-diseased) skeletal muscle (FDB fibers.
Figure 10B:
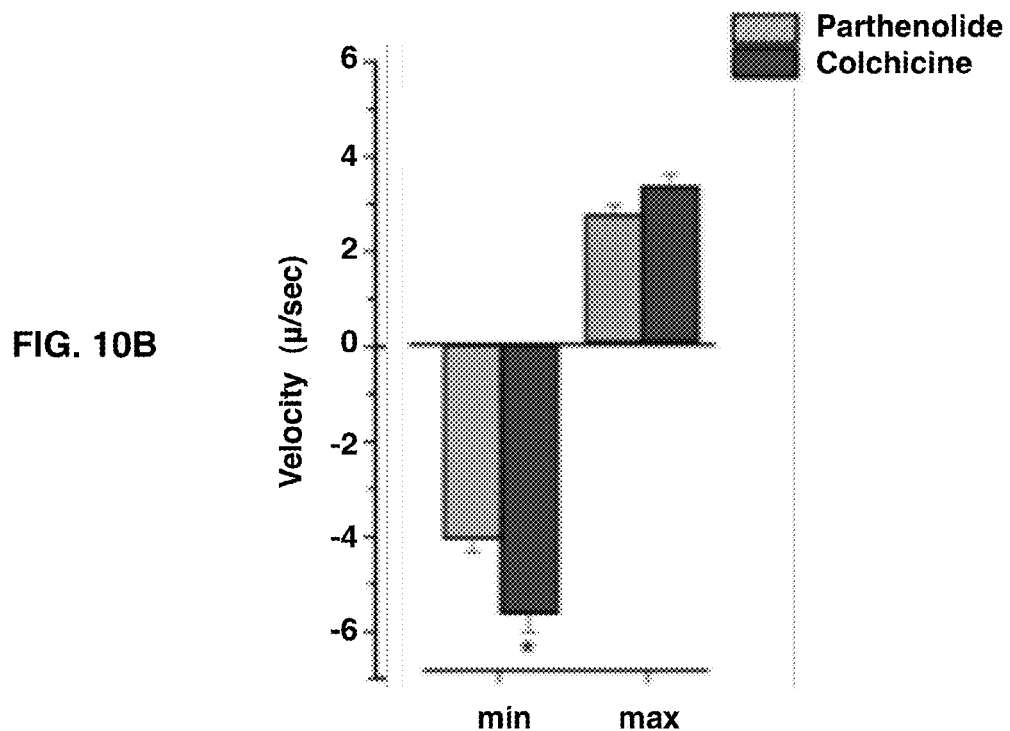
Figure 11:
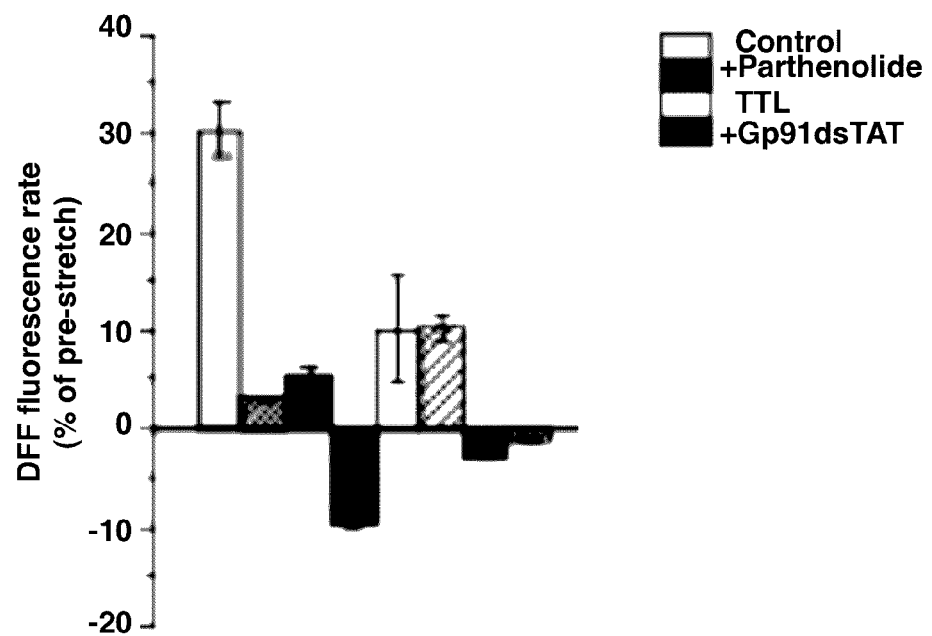
FIG. 11 shows that decreasing Glu tubulin reduced stretch activated ROS production in wild-type FDB muscle fibers. Measures of stretch activated ROS production in wild-type FDB fibers after treatment with parthenolide (10 μM; 2 hrs) or in fibers overexpressing TTL (tubulin tyrosine ligase overexpression to decrease Glu molecularly) both significantly reduced stretch ROS as did Gp91ds-TAT the specific inhibitor of Nox2 activation (1 uM; 2 hrs) Open bars are ROS rate during the period of stretch, hatched bars are ROS rate 10 sec after the release of the stretch. (n=8 per condition; p<0.05; ANOVA).

The present invention shows that in wild-type (non-diseased) skeletal muscle, a significant portion of the a-tubulin network was comprised of post-translational modified (PTM), detyrosinated, a-tubulin and that that Parthenolide treatment in vitro selectively reduced the population of Glu tubulin (FIGS. 9A-9B). As indicated previously, an increase in the detyrosination PTM on a-tubulin was seen in dystrophin deficient and dysferlin deficient muscle. FIGS. 10A-10B show that the Parthenolide targeted decrease in Glu tubulin decreased the mechanical stiffness of the muscle fiber and increased its contraction speed. The Parthenolide targeted decrease in Glu tubulin reduced stretch activated ROS production in wild-type FDB muscle fibers consistent with this PTM playing a critical role in mechano-activation of the X-ROS pathway (FIG. 11).

Figure 12:
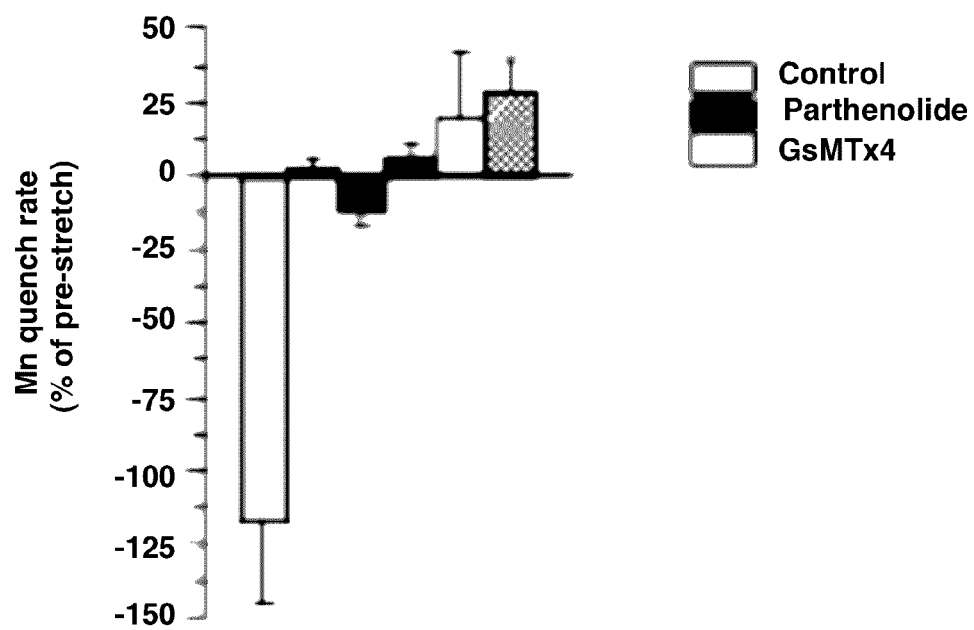
FIG. 12 shows that decreasing Glu tubulin reduced stretch activated calcium influx. Measures of calcium influx, with the Mn quench assay, revealed that in wild-type FDB fibers, parthenolide (10 uM; 2 hrs), or Gp91ds-TAT (1 uM; 30 minutes) inhibited inhibit stretch activated calcium channels. (Open bars are influx rate during the period of stretch, hatched bars are influx rate 10 sec after the release of the stretch). Parthenolide treatment, or the mechano-sensitive channel blocker GsmTx4, significantly reduced stretch activated $Ca^{2+}$ influx. (n=8 per condition; p<0.05; ANOVA).

FIG. 12 shows that Parthenolide targeted decrease in Glu tubulin reduced stretch activated calcium influx consistent with the concept that PTM plays a critical role in mechano-activation of the mechano-sensitive ca2+ influx pathway that is enhanced in muscular dystrophy. In the mdx mouse, in vivo pharmacologic disruption of either Glu tubulin using the parthenolide analog LC-1, or Nox2 activity using in vivo administration of GP91ds-TAT reduced eccentric contraction induced force drop in vivo. These data support the methods of the present invention that targeting either the Nox2 or the microtubules are an effective treatment for muscular dystrophy and potentially for increasing the performance or enhancing injury recovery in healthy muscle.

Figure 13:
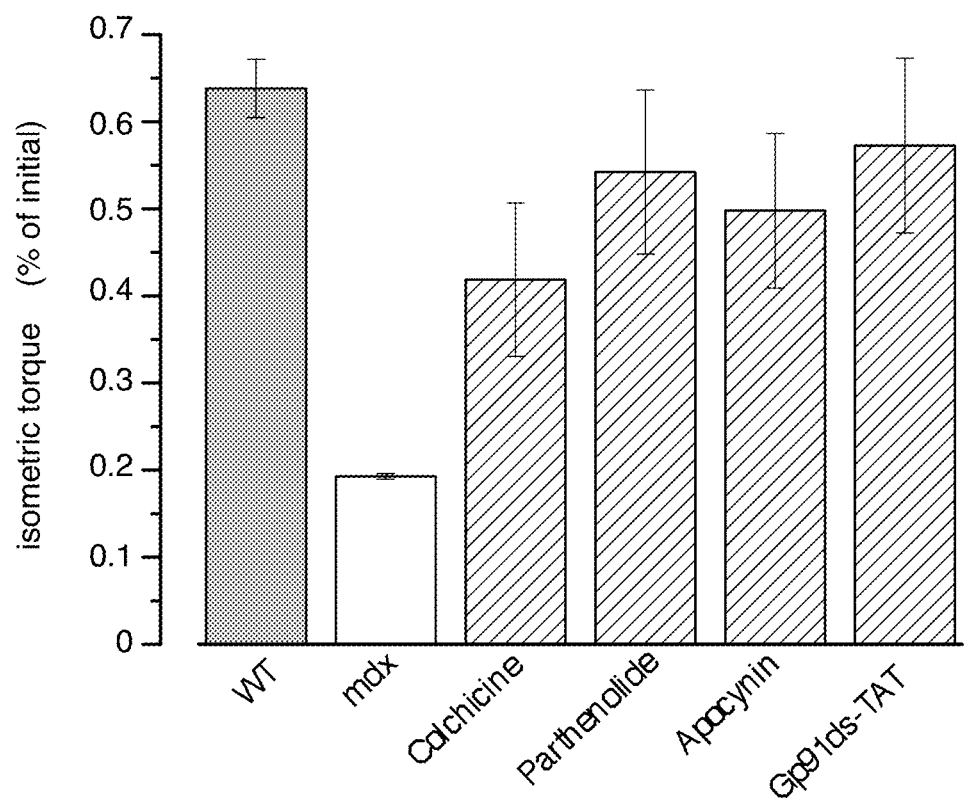
FIG. 13 shows that in the mdx mouse, in vivo pharmacologic disruption of the Glu tubulin structure or Nox2 activity reduced eccentric contraction induced force drop. Using the identical protocol, mdx animals were treated with dimethylaminoparthenolide (parthenolide modified to increase solubility; 50 mg/kg via gavage per day/3 days; n=5) or Gp91ds-TAT (5 ug/g body weight; 2 doses, one day apart; n=3) and tested from resistance to contraction. Each of these paradigms ameliorated the force drop in the mdx. (n=8 per condition; p<0.05 ANOVA; p<0.05 vs mdx; ANOVA).

As previously determined, in vivo treatment of mdx mice with colchicine to target the dense microtubule network or apocynin to inhibit Nox activity significantly ameliorated the contraction induced force drop over 20 eccentric contractions. As shown in FIG. 13, mdx animals treated with dimethylaminoparthenolide or Gp91ds-TAT and tested from resistance to contraction ameliorated the force drop in the mdx, thus indicating therapeutic efficacy.

Discussion

In mdx myofibers (murine DMD), a model of axial stretch was used to illustrate that mechanical stress, transmitted through the microtubule network, activates robust NOX2 dependent ROS production, a pathway termed X-ROS. In contrast to the adult mdx, age matched wild-type or young mdx and wild-type myofibers revealed little or no detectable X-ROS.

The differential magnitude of X-ROS between adult mdx and either adult wild-type or young mdx and wild-type was consistent with both NOX2 subunit content and microtubule network density/protein abundance being elevated in adult mdx myofibers. In fact, activation of X-ROS in the adult mdx was inhibited by either microtubule network destabilization or NOX2 inhibition suggesting both played a role in the significant X-ROS seen in adult mdx. However, the proximate role of the microtubule network in X-ROS activation is supported by the ability to reveal X-ROS upon acute experimentally increasing microtubule network density in young wild-type and mdx myofibers. The acute duration of taxol treatment contradicts any increase in NOX2 subunit or microtubule expression as a contributor to the increase in X-ROS in mdx. Therefore, the increase in microtubule network density is solely sufficient for X-ROS.

In response to experimental membrane stressors, for example, eccentric contraction, acute osmotic challenge, membrane deformation with suction etc., mdx myofibers are unable to maintain a normal low myoplasmic [$Ca^{2+}$] due in large part to increased sarcolemmal $Ca^{2+}$ influx through mechano-sensitive $Ca^{2+}$ channels (7-11). Recently, stretch induced ROS production has been shown to promote dysfunctional $Ca^{2+}$ signaling in mdx muscle due to oxidation of stretch sensitive sarcolemmal $Ca^{2+}$ channels (12, 13). As stretch dependent sarcolemmal $Ca^{2+}$ influx was inhibited with colchicine, GsMTx4 or gp91dsTAT, in the adult mdx, the microtubule network is the critical mechanism that links mechanical stretch to the NOX2 dependent ROS production responsible for sarcolemmal $Ca^{2+}$ channel activation during stretch.

The molecular identity of the stretch sensitive sarcolemmal $Ca^{2+}$ influx channel remains unclear. A report identified the presence of GsmTx4 sensitive mechano-sensitive current density in mdx cells (41) but did not identify a channel involved. Other studies have suggested that a TRPC mechanism is responsible for the increased $Ca^{2+}$ influx in mdx (42) with mechano-sensitive TRPC1 current density being elevated due to Homer down regulation in mdx (43). Protein transcripts for the ROS sensitive (44, 45) SAC and SOCE channels (ORAI-3, TRPC1) are also elevated in DMD samples and Homer 1 transcript being down regulated. Recently, Piezo1 and Piezo2 were identified as multipass transmembrane proteins that form mechanically activated cation channels (46) that can be inhibited by GsMTx4(47). Interestingly, both genes are upregulated in DMD patients as identified in the transcriptome analysis and might take part in X-ROS.

The relative abundance of microtubule and NOX 2 protein subunits in the adult mdx compared to the adult wild-type is indirectly supported by the increase in mRNA transcript in both mdx and human DMD. Notable also is the proximate location of the TGFβ (50) and angiotensin (51) signaling pathways in the network as reports have identified that both signaling cascades act to increase microtubule protein content and network density (52, 53) and are activated in human DMD muscle. Furthermore, inhibition of these pathways is beneficial in both human DMD (54) and in mdx (55).

The potential for X-ROS as a therapeutic target was directly addressed by inhibiting X-ROS components and assaying the protection from contraction induced injury. Colchicine, a potent microtubule depolymerizer, is a FDA approved drug used to prevent gout and to treat Familial Mediterranean Fever (56). In muscle, apocynin, or its oxidation products, have been shown to inhibit translocation of the cytosolic $p47^{phox}$ and $p67^{phox}$ proteins to their membrane fraction counterparts, causing inactivation of NOX (57). While not FDA approved, apocynin is currently in phase 1 clinical trial for the treatment of COPD. In vivo treatment of mdx mice with colchicine or apocynin provided significant protection from both isometric and eccentric injury protocols.

The present invention provides compelling evidence that microtubule dependent X-ROS signaling is a unifying mechanism that links the lack of dystrophin to the enhanced mechano-transduction dependent activation of $Ca^{2+}$ and ROS signaling. Pharmacological targeting of either NOX2 activation or microtubule network stabilization can decrease X-ROS signaling and provide protection from contraction induced injury. Therapies targeting the microtubule cytoskeleton and NOX2 present novel opportunities for intervention in DMD.

The following references are cited herein:
1. Hoffman, et al., 1987. *Cell* 51:919-928.
2. Pegoraro, et al., 2011. *Neurology* 76:219-226.
3. Nishiyama, et al., 2007. *BMC Med Genet* 8:19.
4. Allen et al., 2010. *Canadian jour. of physiology and pharmacology* 88:83-91.
5. Whitehead, et al., 2010. *PLoS One* 5:e15354.
6. Allen, et al., 2010. *Adv Exp Med Biol* 682:297-313.
7. Marchand, et al., 2001. *Cell calcium* 29:85-96.
8. Alderton, et al., 2000. *Trends Cardiovasc Med* 10:268-272.
9. Collet, et al., 2003. *Biophysical journal* 84:251-265.
10. Turner, et al., 1993. *The Journal of membrane biology* 133:243-251.
11. Tutdibi, et al., 1999. *The Journal of physiology* 515 (Pt 3):859-868.
12. Isaeva, et al., 2003. *The Journal of physiology* 547:453-462.
13. Isaeva, et al., 2005. *J Physiol* 565:855-872.
14. Espinosa, et al., 2006. *Journal of cellular physiology* 209:379-388.
15. Hidalgo, et al., 2006. *The Journal of biological chemistry* 281:26473-26482.
16. Whitehead, et al., 2006. *Neuromuscul Disord* 16:845-854.
17. Whitehead, et al., 2006. *Clin Exp Pharmacol Physiol* 33:657-662.
18. Allen, D. 2004 *Clinical and exper. pharmacology & physiology* 31:485-493.
19. Ingber, D. 2008. *J Bodyw Mov Ther* 12:198-200.
20. Stamenovic, et al., 2002. *American journal of physiology* 282:C617-624.
21. Wang, et al., 2001. *Proc. of the National Acad of Sci USA* 98:7765-7770.
22. Wang, et al., 1993. *Science* 260:1124-1127.
23. Prins, et al., 2009. *The Journal of cell biology* 186:363-369.
24. Langevin, et al., 2011. *Journal of cellular physiology* 226:1166-1175.
25. Fernandes, et al., 2005. *Dev Biol* 285:11-27.
26. Best, et al., 1996. *The Journal of biological chemistry* 271:3756-3762.
27. Prosser, et al., 2011. *Science* 333:1440-1445.
28. Iribe, et al., 2009. *Circulation research* 104:787-795.
29. McCain, et al., 2011 *Pflugers Arch* 462:89-104.
30. Rey, et al., 2001. *Circ Res* 89:408-414.
31. Bhandarkar, et al., 2009. *J Clin Invest* 119:2359-2365.
32. Wang, et al., 2005. *Nature cell biology* 7:525-530.
33. Suchyna, et al., 2004. *Nature* 430:235-240.
34. Yeung, et al., 2005. *The Journal of physiology* 562:367-380.
35. Spencer et al., 1997. *J Clin Invest* 99:2745-2751.
36. Ingber, D. E. 2008. *Prog Biophys Mol Biol* 97:163-179.
37. Grange, et al., 2002. *American journal of physiology* 283:C1090-1101.
38. Wolff, et al., 2006. *Muscle & nerve* 34:304-312.
39. Ng, et al., 2008. *American journal of physiology* 295:C146-150.
40. Blaauw, et al., 2008. *Human molecular genetics*.
41. Suchyna, et al., 2007. *The Journal of physiology* 581:369-387.
42. Millay, et al., 2009. *Proceedings of the National Academy of Sciences of the United States of America* 106:19023-19028.

43. Stiber, et al., 2008. *Molecular and cellular biology* 28:2637-2647.
44. Bogeski, et al., 2011. *Cell calcium* 50:407-423.
45. Bogeski, et al., 2010. *Sci Signal* 3:ra24.
46. Coste, et al., 2010. *Science* 330:55-60.
47. Bae, et al., 2011. *Biochemistry* 50:6295-6300.
48. Canato, et al., 2010. *J Biomed Biotechnol* 2010:981945.
49. Defranchi, et al., 2005. *Microsc Res Tech* 67:27-35.
50. Chen, et al., 2005. *Neurology* 65:826-834.
51. Sun, et al., 2009. *J Neurol Sci* 280:40-48.
52. Stroth, et al., 1998. *Brain Res Mol Brain Res* 53:187-195.
53. Hashimoto-Komatsu, et al., 2011. *Hypertens Res* 34:949-956.
54. Ogata, et al., 2009. *J Cardiol* 53:72-78.
55. Cohn, et al., 2007. *Nat Med* 13:204-210.
56. Grody, W. W., and T. Getzug. 2010. *N Engl J Med* 363:2267-2268.
57. Stolk, et al., 1994. *American jour of respiratory cell and mol. biol* 11:95-102.
58. Dorsey, et al., 2011. *Am J Physiol Cell Physiol.*
59. Ziman, et al., 2010. *Biophys J* 99:2705-2714.
60. Anders, S., and W. Huber. 2010. *Genome Biol* 11:R106.
61. Young, et al., 2010. *Genome Biol* 11:R14.

What is claimed is:

1. A method of improving muscular function in an individual, comprising the steps of:
   administering to said individual a pharmacologically effective amount of a compound that inhibits microtubule-dependent NADPH Oxidase 2 reactive oxygen species signaling production;
   administering a pharmacologically effective amount of a compound that blocks sarcolemmal $Ca^{2+}$ channel activation; and
   administering a pharmacologically effective amount of a compound that blocks renin-angiotensin signaling, thereby improving muscular function in said individual.

2. The method of claim 1, wherein the compound that inhibits microtubule-dependent NADPH Oxidase 2 reactive oxygen species signaling production depolymerizes microtubules.

3. The method of claim 2, wherein the compound is selected from the group consisting of colchicine, nocodozole, parthenolide, dimethylaminoparthenolide, 2-phenyl-4-quinolone, polygamain, azaindole, vinca alkaloids, colcemid, or their pharmaceutical salts.

4. The method of claim 3, wherein said compound is colchicine and is administered in an amount from about 5 micrograms/kg to about 20 micrograms/kg of said individual's body weight.

5. The method of claim 1, wherein the compound that inhibits microtubule-dependent NADPH Oxidase 2 reactive oxygen species signaling production is a NADPH Oxidase 2 inhibitor.

6. The method of claim 5, wherein the compound that inhibits NADPH Oxidase 2 is selected from the group consisting of fulvene, apocynin, gp91ds comprising a TAT peptide or other peptide enabling cellular uptake thereof, diphenylene iodonium, and pharmaceutical salts thereof.

7. The method of claim 1, wherein the compound that blocks sarcolemmal $Ca^{2+}$ channel activation is selected from the group consisting of GsMTx4, streptomycin, poloxamer P188, ruthenium red, pyrazole-3, 3,5-bis(trifluoromethyl) pyrazole 2, N-(p-amylcinnamoyl)anthranilic acid,4-Methyl-2-(1-piperidinyl)-quinoline, dantrolene sodium, and SKF 96365, or a pharmaceutical salt thereof.

8. The method of claim 1, wherein the compound that blocks renin-angiotensin signaling is losartan, altace, lisinopril, enalapril, ramparil, zestril, angiotensin converting enzyme inhibitors or a pharmaceutical salt thereof.

9. The method of claim 1, wherein administration occurs before, during or after onset of muscle damage, activity-induced fatigue or muscle fatigue in said individual.

10. A method of treating an individual having a muscular disorder, comprising the steps of:
    administering to said individual a therapeutically effective amount of a compound that inhibits microtubule-dependent NADPH Oxidase 2;
    administering a pharmacologically effective amount of a compound that blocks sarcolemmal $Ca^{2+}$ channel activation; and
    administering a pharmacologically effective amount of a compound that blocks renin-angiotensin signaling, thereby treating said muscular disorder in said individual.

11. The method of claim 10, wherein the compound that inhibits microtubule-dependent NADPH Oxidase 2 reactive oxygen species signaling production depolymerizes microtubules.

12. The method of claim 11, wherein said compound is selected from the group consisting of colchicine, nocodozole, parthenolide, dimethylaminoparthenolide 2-phenyl-4-quinolone, polygamain, azaindole, vinca alkaloids, colcemid, or their pharmaceutical salts.

13. The method of claim 10, wherein the compound that inhibits NADPH Oxidase 2 is selected from the group consisting of fulvene, apocynin, gp91ds comprising a TAT peptide or other peptide enabling cellular uptake thereof, diphenylene iodonium, and pharmaceutical salts thereof.

14. The method of claim 10, wherein the compound that blocks sarcolemmal $Ca^{2+}$ channel activation is selected from the group consisting of GsMTx4, streptomycin, poloxamer P188, ruthenium red, pyrazole-3, 3,5-bis(trifluoromethyl) pyrazole 2, N-(p-amylcinnamoyl)anthranilic acid, 4-Methyl-2-(1-piperidinyl)-quinoline, dantrolene sodium, and an SKF 96365, or a pharmaceutical salt thereof.

15. The method of claim 10, wherein said renin-angiotensin signaling blocker is losartan, or a pharmaceutical salt thereof.

16. The method of claim 10, wherein said muscular disorder is Duchenne Muscular Dystrophy, Becker's Muscular Dystrophy, Congenital Muscular Dystrophy, Limb-Girdle Muscular Dystrophy, Limb-Girdle Muscular Dystrophy-2A, Limb-Girdle Muscular Dystrophy-2B, Limb-Girdle Muscular Dystrophy-2D, Limb-Girdle Muscular Dystrophy-2E, Limb-Girdle Muscular Dystrophy-2l, muscle diseases associated with mutations in the delta.-sarcoglycan gene, Ullrich congenital muscular dystrophy, congenital merosin-deficient 1A muscular dystrophy, myositis, autophagic vacuolar myopathy, myopathies not associated with a specific protein deficiency, myotonic dystrophy type 1, spinal muscular atrophy, critical care myopathy cases, Pompe disease, or sarcoidosis.

* * * * *